(12) United States Patent
Rees

(10) Patent No.: US 7,608,847 B2
(45) Date of Patent: Oct. 27, 2009

(54) SYSTEM AND METHOD FOR IMPLEMENTING A SUSPENDED PERSONAL RADIATION PROTECTION SYSTEM

(76) Inventor: Chet R. Rees, 6403 Prestonshire La., Dallas, TX (US) 75225-2310

( * ) Notice: Subject to any disclaimer, the term of this patent is extended or adjusted under 35 U.S.C. 154(b) by 368 days.

(21) Appl. No.: 11/611,627

(22) Filed: Dec. 15, 2006

(65) Prior Publication Data

US 2007/0138415 A1   Jun. 21, 2007

Related U.S. Application Data

(60) Provisional application No. 60/751,371, filed on Dec. 16, 2005.

(51) Int. Cl.
*G21F 3/02* (2006.01)
*G21F 3/00* (2006.01)

(52) U.S. Cl. ............... 250/516.1; 250/51.15; 2/8.2; 2/9; 2/46; 2/48; 2/117; 2/456; 2/920

(58) Field of Classification Search ............ 250/505.1, 250/515.1, 516.1, 519.1; 2/1, 2.11, 8.2, 9, 2/46–48, 117, 411, 455, 456, 920
See application file for complete search history.

(56) References Cited

U.S. PATENT DOCUMENTS

| | | | |
|---|---|---|---|
| 1,636,419 A | 7/1927 | Hollander | |
| 2,718,598 A | 9/1955 | Graf | 250/58 |
| 2,794,128 A | 5/1957 | Shasky | 250/108 |
| 3,308,297 A | 3/1967 | Mansker | 250/108 |
| 4,254,341 A * | 3/1981 | Herr et al. | 250/519.1 |
| 4,286,170 A | 8/1981 | Moti | 250/515.1 |
| 4,581,538 A | 4/1986 | Lenhart | 250/519.1 |
| 4,654,188 A | 3/1987 | Hankinson | 376/260 |
| D300,945 S | 5/1989 | Fleming et al. | D24/2 |
| 4,932,078 A * | 6/1990 | Jones et al. | 2/70 |
| 5,006,718 A | 4/1991 | Lenhart | 250/519.1 |
| 5,015,864 A * | 5/1991 | Maleki | 250/516.1 |
| 5,115,140 A * | 5/1992 | Rodriguez | 250/516.1 |
| 5,626,540 A * | 5/1997 | Hall | 482/69 |
| 5,704,881 A | 1/1998 | Dudley | 482/69 |
| 5,981,964 A | 11/1999 | McAuley et al. | 250/515.1 |
| 6,281,515 B1 * | 8/2001 | Demeo et al. | 250/516.1 |
| 6,448,571 B1 | 9/2002 | Goldstein | 250/515.1 |
| 6,459,091 B1 * | 10/2002 | DeMeo et al. | 250/516.1 |
| 6,653,648 B2 | 11/2003 | Goldstein | 250/515.1 |
| 6,828,578 B2 * | 12/2004 | DeMeo et al. | 250/519.1 |
| 2005/0211930 A1 * | 9/2005 | DeMeo et al. | 250/516.1 |
| 2007/0138415 A1 * | 6/2007 | Rees | 250/516.1 |

FOREIGN PATENT DOCUMENTS

DE        29 34 955 A1    3/1981

\* cited by examiner

*Primary Examiner*—Bernard E Souw
(74) *Attorney, Agent, or Firm*—Patent Capital Group

(57) ABSTRACT

A personal radiation protection garment that substantially contours to an operator's body is suspended from a suspension means. The garment is operable to protect the operator from radiation. The suspension means is operable to apply constant force. The suspension means allows operator wearing protective radiation garment to move freely in the X, Y, and Z spatial planes simultaneously, such that the protective radiation garment is substantially weightless to operator. A radiation protection face shield and flap can also be suspended from suspension means, such that face shield and flap are substantially weightless to operator. The suspension means can be mounted to a ceiling.

24 Claims, 11 Drawing Sheets

US 7,608,847 B2

SYSTEM AND METHOD FOR IMPLEMENTING A SUSPENDED PERSONAL RADIATION PROTECTION SYSTEM

CLAIMING PRIORITY ON A PROVISIONAL

This application claims priority under 35 U.S.C. §119 of provisional application Ser. No. 60/751371 filed Dec. 16, 2005.

TECHNICAL FIELD OF THE INVENTION

This invention relates in general to medicine and, more particularly, to a suspended personal radiation protection garment.

BACKGROUND OF THE INVENTION

Radiation is used to perform many medical diagnostic and therapeutic tests and procedures. Medical, veterinary, or research personnel may be involved in the performance of such procedures in great numbers and over many years, and are being exposed to scattered radiation as they perform their work. These long-term effects are poorly understood at the present time, but are considered serious enough to warrant mandatory protection to operators in the form of garments or barriers containing materials that absorb a significant proportion of the radiation. In order to properly treat patients, operators require a freedom of motion. Providing a personal radiation protection garment that properly protects operators, while allowing operators to move freely and comfortably presents a significant challenge for medical operators in radiation environments.

SUMMARY OF THE INVENTION

In accordance with the present invention, a method, a system, and an apparatus for implementing a suspended personal radiation protection garment are provided, which substantially eliminate or reduce the disadvantages and problems associated with previous systems, methods, and apparatuses.

In accordance with one embodiment of the present invention, a method for a suspended personal radiation protection device includes providing a garment that substantially contours to an operator's body. The garment is operable to protect the operator from radiation. The garment is suspended from a suspension component.

In accordance with another embodiment of the present invention, a method for a suspended personal radiation protection device includes providing a garment that substantially contours to an operator's body while suspended from suspension component. The suspension component is operable for operator wearing protective radiation garment to move freely in the X, Y, and Z spatial planes simultaneously, such that the protective radiation garment is substantially weightless to the operator. The suspension component is further operable to support the partial weight of the operator, such that the operator can move around in substantially zero gravity or such that the operator bears only a portion of his total weight. The suspension component can be mounted to a ceiling. The suspended personal radiation protection device further includes a face shield, such that the face shield is transparent to visible light allowing operator unhindered vision, and the face shield protects operator from radiation. The suspended personal radiation protection device further includes a flap, such that the flap is operable to protect the operator from radiation between the garment and face shield.

Important technical advantages of certain embodiments of the present invention include supporting the weight of radiation protection garment, face shield, and flap worn by operators. This allows radiation protection garments to be heavier. As a result, radiation protection garments can protect larger areas of operator's body. Radiation protection garments can be thicker to increase X-ray attenuation. More radiation protection reduces operator's risk of cancers, cataracts, and skin damage.

Other important technical advantages of certain embodiments of the present invention include reducing the risk and incidence of musculoskeletal injuries from wearing heavy radiation protection garments. Operators using the present invention have normal freedom of motion as if operator is not wearing heavy material. Furthermore, the present invention allows operator to move about in substantially zero gravity, such that suspension device supports majority of operator's weight, such that operators can work long periods without fatigue.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which.

DETAILED DESCRIPTION OF THE INVENTION

Figure 1:
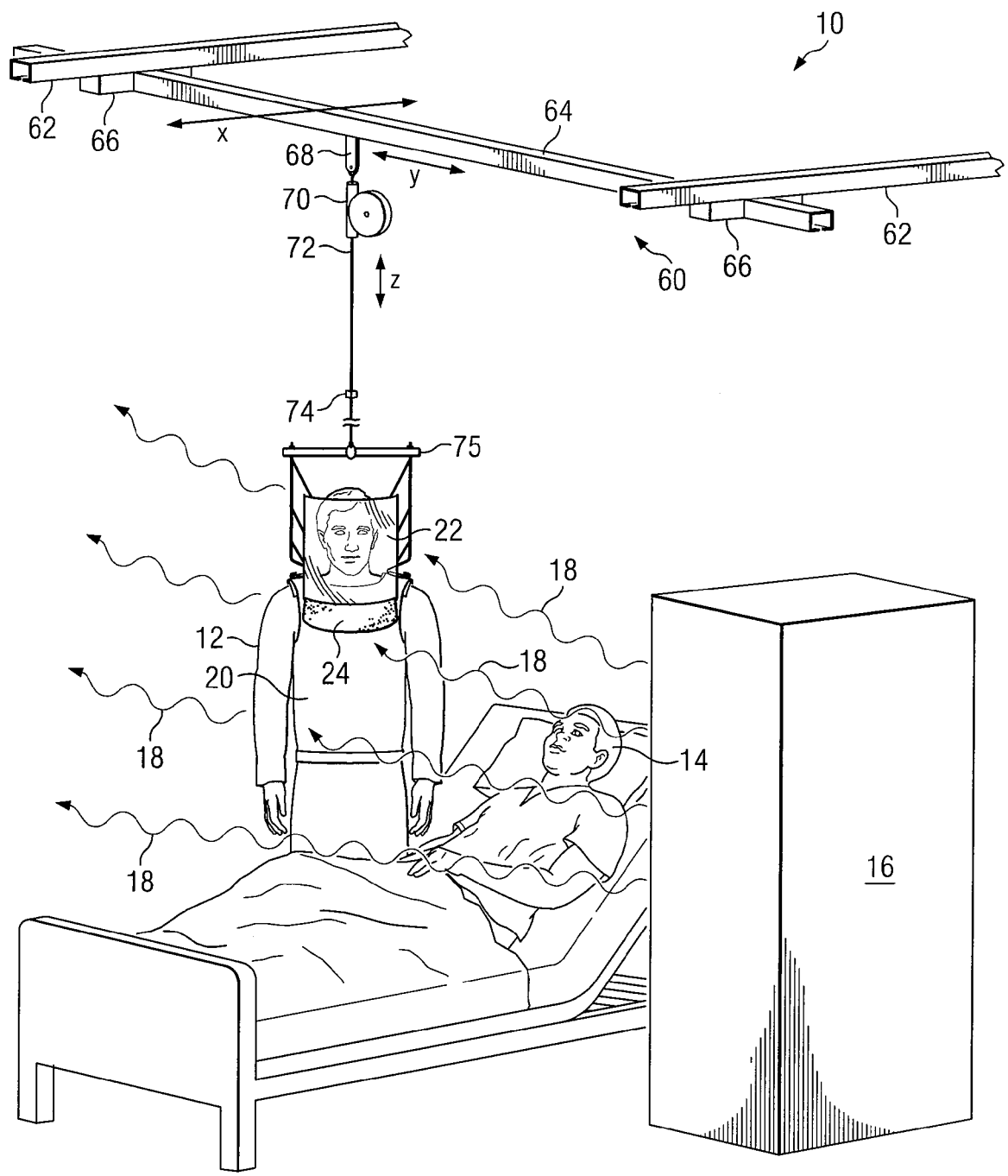
FIG. 1 is a simplified block diagram that illustrates a suspended personal radiation protection system in accordance with a particular embodiment of the present invention.

For purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

Radiation is used to perform many medical diagnostic and therapeutic tests and procedures. The human patient or animal is subjected to radiation using doses as low as possible to enable completion of the medical task, and their exposures are monitored to prevent or reduce risks of significant damage as a result of their exposures. Medical, veterinary, or research personnel may be involved in the performance of such procedures in great numbers and over many years, and are being exposed to scattered radiation as they perform their work. Although their daily exposure is generally less than that for the patient, there are adverse effects of the cumulative, long term exposures to the operators. These long-term effects are poorly understood at the present time, but are considered serious enough to warrant mandatory protection to workers in the form of garments, other garments, or barriers containing materials, generally metallic, that absorb a significant proportion of the radiation. There are a wide variety of such barriers commercially available, and all of them have significant limitations for the operators who must come in close contact with the subject. These operators may be physicians and their assistants, or technically skilled medical personnel, who perform simple or complex medical procedures using their bodies and hands in proximity of the patient, in such positions that scatter radiation from the subject or physical elements in the direct radiation beam will pose significant health risks and unacceptably high exposure readings for the operator if he/she were unprotected.

Risks of radiation exposure at the levels of medical personnel include cancers, cataracts, and skin damage. A review of current protective systems outlines their limitations. Radiation-absorbing walls are useful to contain the radiation to a room, but do not prevent exposures within their confines. Barriers within the room, such as floor or ceiling supported shields, are effective at blocking radiation for personnel who are not in close contact with the radiation field, such as some nurses and technologists, but must be positioned or repositioned frequently when personnel move around the room, and provide cumbersome interference for operators performing the actual medical procedure. They may also be difficult to keep sterile when attempting to use them within the sterile field. The most commonly used protection for operators involves the use of garments containing radiation-absorbing materials, generally lead or other metals, which are worn in the fashion of an garment, or skirt and vest, and do not contaminate the sterile field because they are worn underneath the sterile covering gown. These garments are heavy and uncomfortable, and their long-term usage is known to be associated with diseases of the spine in the neck and back, knee disorders, and other musculoskeletal problems, which can result in disability, medical expenses, and decreased quality of life for the operator. The trade-off between protection and garment weight results in the frequent use of garments that do not cover the legs optimally, and may provide sub optimal radiation protection due to the thickness of the metallic material being limited by the tolerability of the operator. To protect other radiation sensitive tissues such as the corneas of the eye and the thyroid, special heavy glasses containing metallic compounds and a collar around the neck are often worn. Even when the operator is encumbered with these items, the base of the skull, which may contain sensitive bone marrow, and the face are unprotected. Personal face and neck shields address this problem, and are commercially available, but are rarely worn due to their cumbersome nature and heavy weight.

Such problems have been present for many years and there are patents attempting to address them. Modifications to floor-supported mobile shields appear to attempt to provide improved dexterity for the operator relative to the standard bulky mobile barrier, and a floor support system with a modified garment design also attempts the same. However, they still appear to be obstacles to free movement of the operator. A system of barriers around the patient is proposed, but appears expensive, complex, and possibly limiting of operator-patient/subject contact, and frustrating to sterile field operation.

Ceiling mounted barriers around the patient also appear to limit contact between patient and operator, and may make control of sterile field difficult. One configuration includes a ceiling mounted device, which supports the weight of a lead garment, involving a dolly movable in one linear axis, with or without an extension arm that rotates around a central point on the dolly. Such mechanical configurations are in place for other types of suspended barriers, and their motion mechanics may not be well suited for use with something attached to the operator's body, since the operator must frequently move rapidly and freely in all three spatial axes, and will walk in unpredictable and rapid patterns over an operating area of several feet by several feet. One configuration includes the garment being suspended by a simple expansion spring, which will provide uneven forces depending on its degree of expansion occurring with operator motion, due to the nature of its simple spring mechanics. It may also result in harmonic motions that affect operator dexterity. In addition, failure of the spring due to cycle stresses could lead to the operator injury in the design as depicted in the patent. Also, location of the spring in a vertical direction above the operator could result in limitations due to ceiling height. Integration of the system with the heavy image intensifier monitor screen as suggested could further encumber the operator from normal motion.

A discussion of the types of motion performed by operators during their work is relevant. Operators are generally standing next to an operating table where the patient is positioned. They often reach over the patient to various parts of the body, and they may lean forward while reaching. This puts great stress on the spine when heavy garments are worn. They may bend or stoop to small degrees, but rarely excessively because the workspace containing the patient and all the tools are located at a height requiring minimal vertical motion. In addition, most procedures involve a sterile field where the operator's hands, arms, and torso from neck to waist must remain confined, so excessive vertical motion is not allowed. The operator may move considerably in the X and Y plane, which is horizontal and parallel to the floor, by walking or turning their body. The operator requires freedom of motion in these directions.

Overhead cranes have been available for many years and are commonly employed in the materials handling industry. The following is a description of a bridge crane. A bridge crane includes at least one bridge, a trolley moving on the bridge, end trucks arranged at the ends of the main bridge to support the main bridge, wheels arranged to the end carriages intended to move along substantially parallel rails substantially parallel to the end trucks and on the other hand substantially transverse in relation to the main bridge and thus to support the entire crane on the rails, while slides have been arranged between one end truck and the corresponding end of the main bridge allowing a longitudinal movement of the end truck in relation to the main bridge and a rotation of the end truck and main bridge in relation to each other.

Smaller cranes such as might be used to support a load up to 250 pounds, are often operated by workers without the aid of motorized assistance, since the crane's movable parts are light enough to be manipulated by hand. Different systems are employed to suspend the load from the cranes, including hoists, balancers, and intelligent assist devices.

Tool balancers are also currently available and help to suspend tools in the workspace in a manner that provides ergonomic benefit for workers using them. The tool balancer is generally attached overhead the workspace, and reels out cable from which the tool is suspended. Adjustments may be made to provide a "zero gravity" balancing of the tool at the desired height, such that the worker may move the tool up or down within a working range without having to bear a significant portion of the tool's weight. Different adjustment may cause the tool balancer to exert a stronger upward force such that the operator must apply a downward force on the tool to pull it down to the workspace, and the balancer will cause the tool to rise when the operator releases it. Tool balancers may be of the spring or pneumatic variety, referring to the mechanism, which provides the force for its operation. A spring tool balancer, such as in the preferred embodiment of this invention, generally contains a coiled flat spring, similar to a clock spring, which is attached to a reel with a conical shape and serves as the platform for the winding of the cable. The conical shape provides a variable mechanical advantage, which offsets the variance of the force provided by the spring as it winds or unwinds. The result is a relatively constant force on the cable within a definable working range.

Safety concerns mainly involve falling objects, strength of the suspension device, strength of the cable, and operator falls.

The balancer is attached to the trolley by its own hook and a safety chain. The suspension device is commercially available at specified maximum loads, which include a wide safety margin. The mounting of the suspension device will be done according to architectural standards.

Detachment of the garment from the suspension system will require certain care. A cable stop will prevent the hanger from going higher than the set level. The worker could stand on a step stool and remove the garment without concern for sudden upward, uncontrolled motion of the balancer cable and hanger. In another method of detachment, the hanger could be gripped firmly as another person detaches the garment suspension cables from the hanger, and the hanger could then be slowly raised until the cable stop engages the spring balancer. Alternatively, a weight, which is approximately equivalent to the weight of the garment, could be attached to the hanger prior to disengaging the garment. This will drop the garment and require it to be supported by the worker, who may then disengage it from the hanger. The weight will prevent any upward motion of the hanger in an uncontrolled manner. The next time the garment is attached, the weight could be removed after secure attachment of the garment is confirmed.

For most operation, the garment need not be detached from the cable. It could be left suspended and moved out of the way of other activities. Another alternative method would involve setting the force on the balancer to be slightly greater than the weight of the garment. Once removed from the body, the garment would then slowly and safely rise up until stopped by the cable stop. Upon next use, it could easily be pulled back down into position.

Annual inspections of the system may be performed for cable frays, hook lock malfunctions, and rail component flaws.

In the event of an operator fall, it is unlikely that the system will contribute to operator harm since the balancer cable is long enough to allow the operator to reach the floor. Any harm to the operator should be the same as if not attached to the cable, except perhaps for some beneficial effect of the upward force of the suspension system.

In the event that rapid detachment of the operator from the system is necessary due to emergency, this can be achieved by simple removal of the garment from the body without detachment from the system. The garment can be left hanging, and the suspended garment can be moved to the end of the runway, clear of the moving patient or stretcher.

FIG. 1 is a simplified block diagram of a suspended personal radiation protection system 10. System 10 includes an operator 12, a patient 14, a radiation source 16, radiation 18, a suspension device 60, a hanger 75, a personal radiation protection garment 20, a face shield 22, and a flap 24. Suspension device 60 includes rails 62, a bridge 64, end trucks 66, a trolley 68, a balancer 70, a cable 72, and a cable stop 74. Other architectures and components of system 10 may be used without departing from the scope of this disclosure.

In general, garment 20, shield 22, and flap 24 suspend from hanger 75, which suspends from suspension device 60. Operator 12 positions himself into suspended garment 20, shield 22, and flap 24, such that operator 12 is not supporting the weight of garment 20, shield 22, and flap 24. While using radiation 18 to treat patient 14, operator can move freely in the X, Y, and Z spatial planes, such that garment 20, shield 22, and flap 24 are substantially weightless.

In accordance with the teachings of the present invention, suspended personal radiation protection system 10 achieves an effective way for operators 12 to protect themselves properly and comfortably from harmful radiation. garment 20, shield 22, and flap 24 are operable to protect operator from harmful radiation. Suspension device 60 and hanger 75 are operable to suspend garment 20, shield 22, and flap 24, such that operator 12 is not hindered or burdened by the weight from garment 20, shield 22, and flap 24. Operator 12 is able to freely move around in all three axes while garment 20, shield 22, and flap 24 are substantially contoured to operator's body.

System 10 offers advantages to operators 12 who work with radiation. This is due, at least in part, to the suspended personal radiation garment 20, shield 22, and flap 24, which protects operator 12 from harmful radiation 18 during fluoroscopically guided operations. For example, operator 12 has complete freedom of motion in the X, Y, and Z planes while the personal radiation protection garment 20, shield 22, and flap 24 are substantially contoured to operator's body. The suspended personal radiation protection system 10 allows operator to have complete freedom of motion commonly used during medical and research procedures. Furthermore, operator can remain sterile while using the suspended personal radiation protection garment 20, shield 22, and flap 24. Details relating to these operations are explained below in FIG. 1 and FIG. 2.

Operator 12 may include any individual desiring to wear a personal radiation protection garment 20 in a medical environment, veterinary environment, or research environment. Operator may include an individual who perform simple or complex medical procedures involving radiation 18, such that operator's body and hands are in proximity of patient 14, such that scatter radiation 18 from patient 14 or physical elements in the direct radiation beam will pose significant health risks. Health risks to operator 12 may include cancers, cataracts, and skin damage. For example, operator 12 may include physicians, assistants, or technically skilled medical personnel during fluoroscopically guided operations. The personal suspended radiation protection garment 20, shield 22, and flap 24 allow operator 12 to move freely during fluoroscopically guided operations while providing protection from harmful scatter radiation 18.

Patients 14 may include a human or animal involved in a simple or complex medical procedure involving radiation 18. Patient 14 is subjected to radiation 18 doses as low as possible to complete the medical task, and the patient's exposures are monitored to reduce risks of significant damage from the radiation. In another embodiment, patient 14 may include an inanimate object involved in a simple or complex procedure involving radiation 18.

Radiation source 16 may include any device emitting radiation 18. For example, in medical procedures, radiation sources may include x-ray machines, nuclear medicine, and devices used for radiation therapy. Radiation source 16 can be any device emitting radiation 18.

Radiation 18 may include ionized radiation or non-ionized radiation. Radiation 18 may be man-made radiation or radiation from another source. Some of the major isotopes may include I-131, Tc-99m, Co-60, Ir-192, and Cs-137. In medical procedures, radiation 18 may be emitted from x-ray machines, nuclear medicine, and radiation therapy devices. For example, some parts of the original x-ray beam intercepted by patient, or by another individual or object, may become scattered and change direction, such that operator 12 will absorb some harmful scattered radiation beams 18.

Suspended personal radiation protection garment 20 may contain radiation-absorbing materials, such as lead or other metals. Suspended personal radiation protection garment 20 can be thicker and heavier than traditional radiation protection garments, because operator does not support the weight of the suspended personal radiation protection garment 20. Additionally, suspended personal radiation protection garment 20 can cover more of operator's body, such as operator's arms and legs. Suspended personal radiation protection garment 20 suspends from hanger 75, which suspends from suspension device. Suspended personal radiation protection garment 20 can substantially contour to operator's body while garment suspends from hanger, such that hanger supports the weight of garment. Suspended personal radiation protection garment 20 allows operator to move freely in the X, Y, and Z planes simultaneously, such that operator 12 can move normally as if operator 12 is not wearing a heavy radiation protection garment 20. Suspended personal radiation protection garment 20 allows operator 12 to wear sterile gloves and gown in the usual manner. Details relating to the suspension device 60 are explained below in FIG. 1. Details relating to the garment 20 are explained below in FIG. 2.

Materials and/or components may be included in suspended personal radiation protection garment 20 in order to achieve the teachings of the protective, free moving, and weightlessness features of the present invention. However, due to its flexibility, suspended personal radiation protection garment 20 may alternatively be equipped with (or include) any suitable component or material, or any other suitable element or object that is operable to facilitate the operations thereof. Considerable flexibility is provided by the structure of suspended personal radiation protection garment 20 in the context of suspended personal radiation protection system 10 and, accordingly, it should be construed as such.

Suspended personal radiation protection face shield 22 may contain radiation-absorbing materials, such that face shield attenuates X-rays, but is transparent to visible light allowing operator unhindered vision. Suspended personal radiation protection face shield 22 can be heavier and curve or bend around to cover more of operator's face than traditional radiation protection face shields, because operator 12 does not support the weight of the suspended personal radiation protection face shield 22. The suspended personal radiation protection face shield 22 protects operator 12 from radiation approaching from the sides of operator's face. The operator can wear normal corrective optical lenses behind face shield 22. Suspended personal radiation protection face shield 22 suspends from hanger 75, such that hanger 75 supports the weight of face shield 22. Suspended personal radiation protection face shield 22 allows operator to move freely in the X, Y, and Z planes simultaneously, such that operator 12 can move normally as if operator 12 is not wearing a heavy radiation protection face shield 22. Suspended personal radiation protection face shield 22 may be attached to hanger 75 with a plurality of ropes or wires or rigid rod systems. Details relating to the suspension device 60 are explained below in FIG. 1. Details relating to the face shield 22 are explained below in FIG. 2.

Suspended personal radiation protection flap 24 may contain radiation-absorbing materials, such as acrylic lead or other metals. Suspended personal radiation protection flap 24 can be a softer fabric material, such that flap 24 covers the neck area not protected from garment 20 and shield 22. Suspended personal radiation protection flap 24 can be thicker and heavier than traditional radiation protection flaps 24, because operator 12 does not support the weight of the suspended personal radiation protection flap 24. Additionally, suspended personal radiation protection flap 24 can protect more of operator's neck and thyroid area. Suspended personal radiation protection flap 24 suspends from shield 22, which suspends from hanger 75. Suspended personal radiation protection flap 24 allows operator 12 to move freely in the X, Y, and Z planes simultaneously, such that operator 12 can move normally as if operator 12 is not wearing a heavy radiation protection flap 24. Details relating to the suspension device 60 are explained below in FIG. 1. Details relating to the flap 24 are explained below in FIG. 2.

In another embodiment, suspended personal radiation protection shield 22 and flap 24 can be integrated, such that one piece is formed. In another embodiment, suspended personal radiation protection garment 20, shield 22, and flap 24 can be integrated, such that one piece is formed. In another embodiment, suspended personal radiation protection garment 20, shield 22, and flap 24 can be integrated with hanger 75, such that one piece is formed.

Rails 62 can be permanently affixed to ceiling support structures over the area of operator's workplace. Rails 62 may run parallel with one another, such that rails 62 represent the length of the X-axis that operator 12 can move freely within while wearing the suspended personal radiation protection garment 20, shield 22, and flap 24. The interior of rails 12 can include a runway, such that rollers attached to end trucks 66 can slide along the rail runways. Details relating to rollers and runways are below in FIG. 6.

Bridge 64 can be positioned perpendicular between rails 62 over the area of operator's workplace. Bridge 64 represents the length of the Y-axis that operator 12 can move freely within while wearing the suspended personal radiation protection garment 20, shield 22, and flap 24. Bridge 64 is affixed to rails 12 and movable along rails 12 by an end truck 66 on each rail 12. Bridge 64 can include a runway, such that roller attached to trolley 68 can slide along bridge runway.

End trucks 66 allow bridge 64 to move along rails 62. End trucks 66 can be attached to bridge 64, such that only a small motion is permitted along bridge 64. This small motion allows slight imperfections in suspension device 60, such that bridge 64 movement along rail runways is smoother. End trucks 66 can include rollers to slide within rail runways, such that bridge 64 moves along rail runways via end truck rollers. The bridge 64 is freely movable along the X-axis of rails 62. The length of the X-axis spatial movement of bridge 64 can be limited to the ends of rail runways, such that end stops prevent further movement.

Trolley 68 can include roller, such that trolley roller is positioned in bridge runway. The trolley is 68 freely movable along the Y-axis of bridge 64. The length of the Y-axis spatial movement of trolley 68 can be limited to the ends of bridge runway, such that end trucks prevent further movement. Trolley 68 can attach to balancer 70, which suspends personal radiation protection garment 20, shield 22, and flap 24, such that operator 12 can move freely in the X and Y spatial planes defined above by the length of the rails 62 and the length of the bridge 64. The plane defined by the X and Y spatial axes is designed to correspond to operator's desired work area on the floor. Operator 12 wearing suspended personal radiation protection garment 20, shield 22, and flap 24 has very smooth and facile motion within this plane. In another embodiment of this invention, a telescoping component on bridge 64 can allow extension of trolley 68 farther than the length of the bridge 64, such that the Y spatial axis is greater for operator 12 to freely move within the X, Y plane.

In another embodiment, suspension device 60 can include linear motion devices or any other suitable means for allowing bridge 64 and trolley 68 to move freely. For example, linear motion devices are operable for roller bearings to roll inside guides, such that facile motion is allowed. Trolley 68 can include roller bearings operable to roll inside a guide included in bridge 64, such that facile motion in Y-axis is allowed. End trucks 66 can include roller bearings operable to roll inside a guide included in rails 62, such that facile motion in X-axis is allowed. Suspension device 60 is operable by any suitable means to allow free motion in the x and y axes for operator 12 wearing suspended personal radiation protection garment 20, shield 22, and flap 24.

Balancer 70 may be a spring balancer 70 attached to trolley 68 by a hook, and a safety chain or cable for the event of hook failure. Spring balancer 70 applies constant and controllable uplifting force on garment 20, shield 22, and flap 24. Spring balancer 70 can include a coiled flat spring, similar to a clock spring, attached to a reel with a conical shape. The conical shape provides a variable mechanical advantage, which offsets the variance of the force provided by the spring as it winds or unwinds, such that there is a relatively constant force on cable within a definable working range. Spring balancer 70 allows operator 12 wearing suspended personal radiation protection garment 20, shield 22, and flap 24 freedom of motion in the vertical Z-axis spatial plane. Operator 12 wearing the heavy and bulky garment 20, shield 22, and flap 24 can freely perform vertical motion activities, such as stooping, leaning, squatting, standing on an elevated surface. The tension can be designed to provide optimum relief of garment's weight for operator, and this force can be constant in all positions by operator 12. Spring balancer 70 applies a constant force to oppose the weight regardless of how much cable 72 is extended.

In another embodiment, balancer 70 can be counterweights 70 attached to trolley 68 by a hook, and a safety chain or cable for the event of hook failure. Counterweights 70 apply constant and controllable uplifting force on garment 20, shield 22, and flap 24. Counterweights 70 allow operator wearing suspended personal radiation protection garment 20, shield 22, and flap 24 freedom of motion in the vertical Z-axis spatial plane. Operator 12 wearing the heavy and bulky garment 20, shield 22, and flap 24 can freely perform vertical motion activities, such as stooping, leaning, squatting, standing on an elevated surface. The tension can be designed to provide optimum relief of garment's weight for operator 12, and this force can be constant in all positions by operator 12. Counterweights 70 apply a constant force to oppose the weight regardless of how much cable 72 is extended.

In another embodiment, balancer 70 can be a constant force spring 70 attached to trolley 68 by a hook, and a safety chain or cable for the event of hook failure. Constant force spring 70 applies constant and controllable uplifting force on garment 20, shield 22, and flap 24. Constant force spring 70 allows operator 12 wearing suspended personal radiation protection garment 20, shield 22, and flap 24 freedom of motion in the vertical Z-axis spatial plane. Operator 12 wearing the heavy and bulky garment 20, shield 22, and flap 24 can freely perform vertical motion activities, such as stooping, leaning, squatting, standing on an elevated surface. The tension can be designed to provide optimum relief of garment's weight for operator 12, and this force can be constant in all positions by operator. Constant force spring 70 applies a constant force to oppose the weight regardless of how much cable 72 is extended.

In other embodiments, balancer 70 can include a pneumatic balancer 70, an air balancer 70, a spring motor arrangement 70, an intelligent assist device 70, or any other system, which provides a counterbalancing function or suspension system for the suspended personal radiation protection garment 20, shield 22, and flap 24.

In another embodiment of this invention, servomechanisms can be used to provide near effortless control and rapid response of the suspension device to bodily motions. The servo mechanics may be incorporated into all axes, or simply into the vertical motion axis alone. The servo apparatus will have motion sensors that detect operator movement, and can stimulate power assisted motion and cessation of motion, minimizing the effort of the operator to move the system, and also minimizing any tendency of the system to move operator 12 after the operator stops moving. The power motion is achieved by means of motors in conjunction with belts, chains, or cables along the desired axes along rails 62.

In another embodiment, balancer 70 is mounted horizontally along bridge 64 rather than hanging vertically. The balancer 70 mounted horizontally provides more headroom for operator 12 in a low ceiling or low suspension environment. A pulley can be included over operator's head that can enable suspension device to create a constant force, such that operator does not feel the weight of the suspended personal radiation protection garment 20, shield 22, and flap 24.

In another embodiment, the suspension force of balancer 70 can be adjusted to be greater than the weight of protective garment 20, shield 22, and flap 24, such that balancer can support a portion or all of operator's body weight. This provides added relief of the burden on the operator's spine, hips, knees, and other support structures during long procedures. A specialized harness system is incorporated into garment 20 utilizing straps and pads around the chest, torso, or thighs. This harness is integrated into the garment 20 in such a way that the support system will result in reduction in weight of the not only the garment 20 upon the operator 12, but the harness also can support a portion or all of the operator's weight. The suspended garment 20 becomes part of the suspension system and reduces the weight of operator 12 to some degree. The harness system can include a rigid seat-like apparatus. Details relating to the harness are explained below in FIG. 3.

Cable 72 is suspended from balancer 70 and attaches to hanger 75. In other embodiments, cable 72 may also include a rope or a belt. Cable 72 is several feet long and allows operator 12 to move extensively in the vertical Z-axis. Cable 72 also allows operator 12 to freely move slightly outside the perimeter of the plane formed by the X and Y axes. Cable 72 can include a swivel mount that permits free rotation of the cable suspension mechanism allowing operator 12 to twist as needed. This may include a swivel hook or snap that connects the cable 72 to hanger 75. Cable 72 is operable to safely hold the amount of weight and force caused by the suspended personal radiation protection garment 20, shield 22, and flap 24.

Cable stop 74 is a device attached to cable 72 operable to prevent hanger from going higher than the set level. Cable stop 74 will engage the balancer 70, such that cable stop 74 and hanger 75 are prevented from moving too high. For example, operator 12 can remove suspended personal radiation protection garment 20 as another individual firmly grips hanger 75, and hanger 75 could be slowly raised until the cable stop 74 engages balancer 70.

Hanger 75 is operable to suspend personal radiation protection garment 20, shield 22, and flap 24. Hanger 75 is attached to cable 72. Hanger 75 is positioned above operator's head to avoid collision with operator's head during manipulations. Personal radiation protection garment 20, shield 22, and flap 24 can be removed from hanger 75, attached to hanger 75, and remain suspended from hanger 75 indefinitely. For example, garment 20 can rest on the hanger 75 similar to a clothes hanger, such that garment 20 is not resting on operator's body. Shield 22 and flap 24 can be suspended from hanger 75 by ropes, wires, cables or any other suitable means. Hanger 75 can take on several embodiments.

Figure 2A:
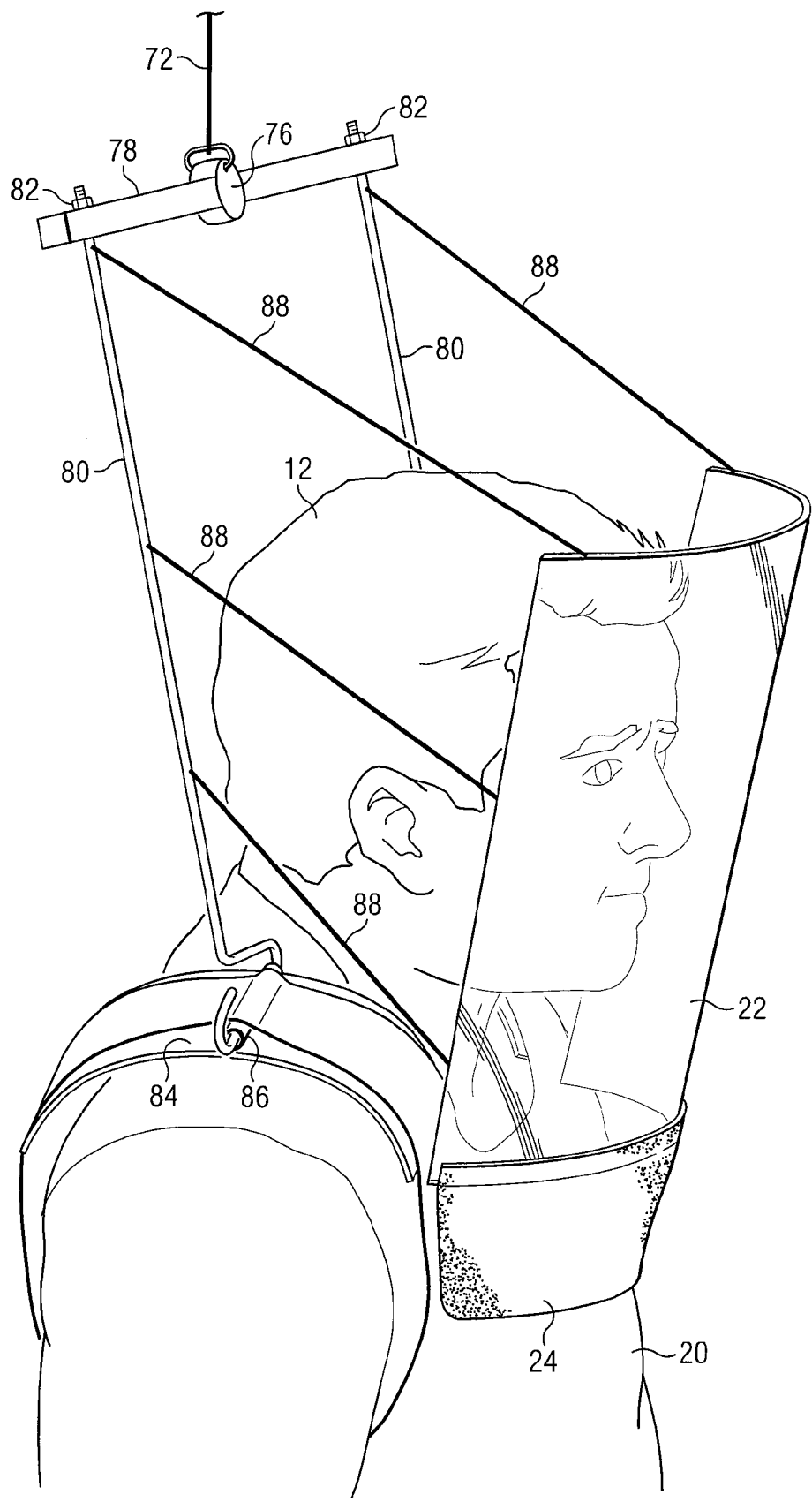
FIG. 2A is a simplified block diagram that illustrates a side view of a hanger suspending a personal radiation protective garment, shield, and flap in accordance with a particular embodiment of the present invention.
Figure 2B:
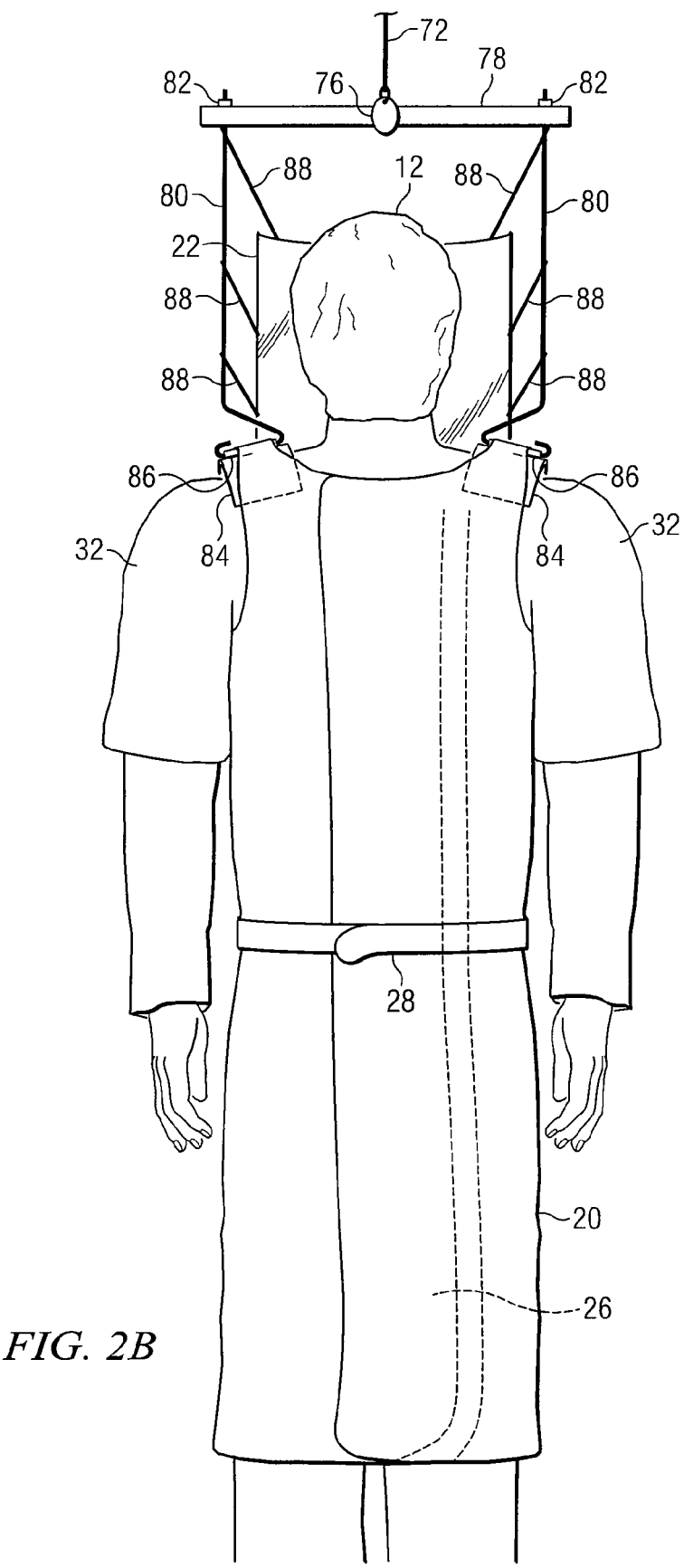
FIG. 2B is a simplified block diagram that illustrates a rear view of a hanger suspending a personal radiation protective garment, shield, and flap in accordance with a particular embodiment of the present invention.
Figure 2C:
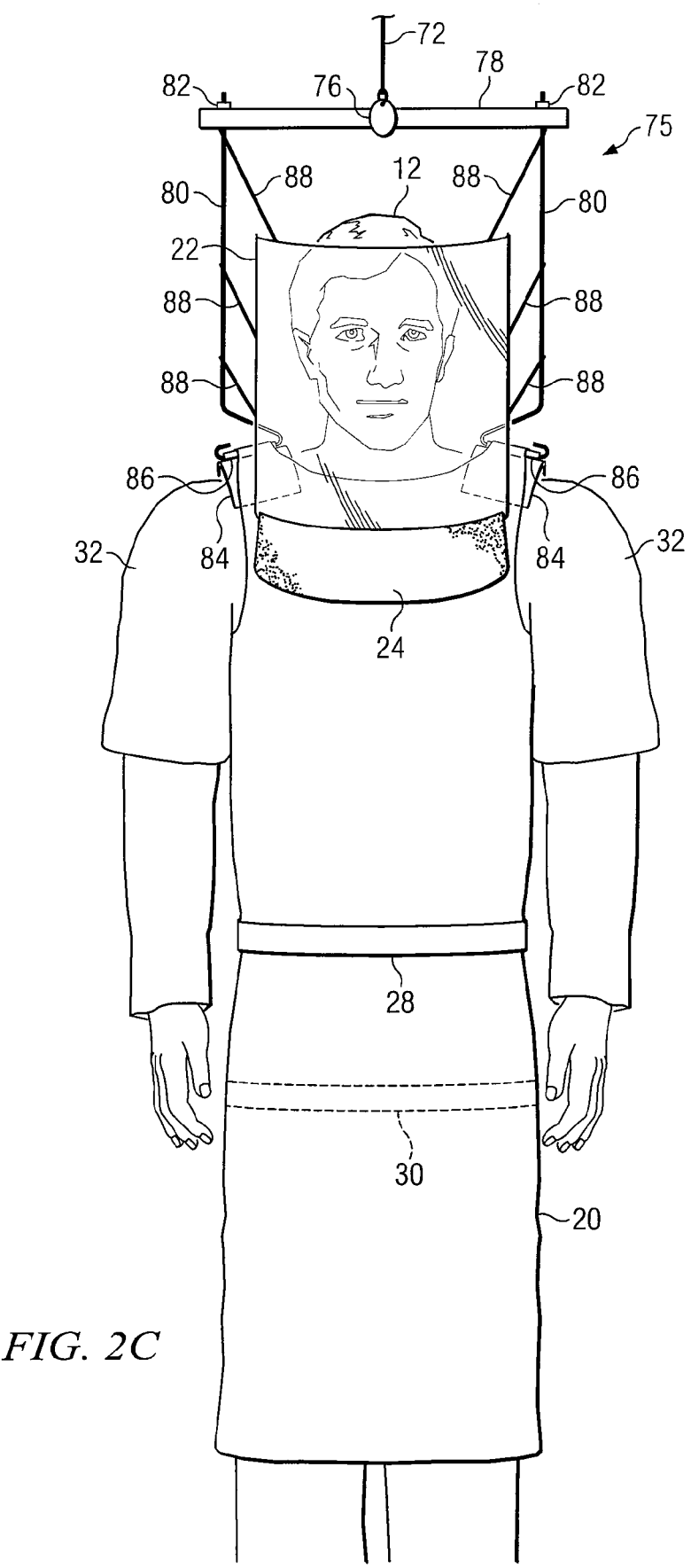
FIG. 2C is a simplified block diagram that illustrates a front view of a hanger suspending a personal radiation protective garment, shield, and flap in accordance with a particular embodiment of the present invention.

FIGS. 2A, 2B, and 2C are simplified block diagrams of personal radiation protection garment 20, shield 22, and flap 26 suspending from hanger 75. Suspended personal radiation protection device includes garment 20, shield 22, flap 24, and hanger 75. Garment 20 includes fastening means 26, belt 28, Velcro for adjustable layer 30, and sleeve 32. Hanger includes widget 76, cross bar 78, drop rod 80, nut 82, shoulder plate 84, plate sleeve 86, and shield support cables 88.

Suspended personal radiation protection garment 20 may contain radiation-absorbing materials, such as lead or other metals. Suspended personal radiation protection garment 20 can be thicker and heavier than traditional radiation protection garments, because operator 12 does not support the weight of the suspended personal radiation protection garment 20. Additionally, suspended personal radiation protection garment 20 can cover more of operator's body, such as operator's arms and legs. Suspended personal radiation protection garment 20 suspends from hanger 75, which suspends from suspension device 60. Suspended personal radiation protection garment 20 can substantially contour to operator's body while garment 20 suspends from hanger 75, such that hanger 75 supports the weight of garment 20. Suspended personal radiation protection garment allows operator 12 to move freely in the X, Y, and Z planes simultaneously, such that operator 12 can move normally as if operator 12 is not wearing a heavy radiation protection garment 20. Suspended personal radiation protection garment 20 allows operator 12 to wear sterile gloves and gown in the usual manner.

Fastening means 26 of garment can be positioned in front, side, or rear of garment 20. Garment 20 can be opened and closed by Velcro, buckles, or any suitable fastening means 26 for attaching two pieces of a heavy material together. For example, if suspended garment 20 has fastening means 26 on the rear of garment 20, then operator 12 can walk up to suspended garment 20 and garment 20 will be suspended over operator 12 for usage. An assistant can fasten the Velcro or buckles, such that operator 12 can quickly and effortlessly receive protection of the suspended personal radiation protection garment 20 that is substantially contoured to operator's body. Operator 12 can wear a sterile gown and sterile gloves in the normal manner.

Belt 28 on garment 20 includes Velcro, buckle, or fastening means, such that belt helps garment stay closed. Belt 28 can be fastened on the front, side, or rear of garment 20. Belt 28 also helps suspended personal radiation protection garment 20 substantially contour to operator's body, such that operator's body is properly protected.

Velcro, buckle, or fastening means for adjustable garment layer 30 allows operator to adjust the length of suspended personal radiation protection garment 20. For example, a short person can fold up the excess garment material and fasten the garment 30, such that the bottom part of the garment is double-layered. Similarly, a tall person can unfasten the double layered area of the garment 20 to receive more radiation protection on legs, such that the suspended personal radiation garment 20 hangs to the operator's feet.

Sleeve 32 can be on left or right arm, and sleeve 32 may contain radiation-absorbing materials, such as lead or other metals. Sleeve 32 allows more protection coverage of operator's body, because operator does not support the weight of the suspended sleeve 32.

Hanger 75 is operable to suspend the personal radiation protection garment 20, shield 22, and flap 24. Hanger 75 is attached to cable 72. Hanger 75 is positioned above operator's head to avoid collision with operator's head during manipulations. Personal radiation protection garment 20, shield 22, and flap 24 can be detached to hanger 75, attached to hanger 75, and remain attached to hanger 75 indefinitely. For example, garment 20 can rest on the hanger similar to a clothes hanger, such that garment 20 is not resting on operator's body. Shield 22 and flap 24 can be suspended from hanger 75 by ropes, wires, cables or any other suitable means.

Widget 76 connects hanger to cable. Widget 76 can be a hook, a pulley, or any suitable means to attach hanger 75 to cable 72. Widget 76 is made of material that can support a minimum weight of the suspended personal radiation protection garment 20, shield 22, and flap 24. Pulley widget 76 allows operator 12 to bend sideways, such that pulley widget 76 moves along hanger 75 to properly distribute weight. Details relating to pulley widget 76 are explained below in FIG. 5.

Cross bar 78 attaches to cable 72 via widget 76. Cross bar 78 is made of material that can support at least a minimum weight of the suspended personal radiation protection garment 20, shield 22, and flap 24. Cross bar 78 is positioned above operator's head to avoid collision with operator's head during manipulations. Cross bar 78 can include grooves where widget 76 attaches, such that weight is properly distributed when operator 12 leans forward or backward.

Drop rod 80 attaches to cross bar 78 and is held in place with a nut 82. Drop rod 80 is made of material that can support at least a minimum weight of the suspended personal radiation protection garment 20, shield 22, and flap 24. Drop rod 80 can attach to shoulder plate 84 in various embodiments. In one embodiment, drop rod 80 can be angled inward, such that drop rod 80 is inserted into shoulder plate sleeve 84 closer to operator's neck. This particular embodiment is effective at distributing weight and supporting the suspended garment 20, shield 22, and flap 24.

Shoulder plate 84 is suspended by hanger 75. Shoulder plate 84 is made of material that can support at least a minimum weight of the suspended personal radiation protection garment 20, shield 22, and flap 24. Shoulder plate 84 can be one piece that extends over both shoulders or shoulder plate 84 can be two pieces, such that each shoulder plate 84 is positioned over operator's shoulders. Suspended personal radiation protection garment 20 can be placed on shoulder plate 84, such that shoulder plate 84 supports the weight of garment 20. Shoulder plates 84 can be positioned slightly above operator's shoulders, such that shoulder plates 84 act as a substitute for operator's shoulders while the garment 20 is still substantially contoured to operator's body.

Plate sleeve 86 can be welded or affixed to shoulder plate 84. Plate sleeve 86 is operable for hanger to be inserted, such that plate sleeve 86 securely attaches shoulder plate 84 to hanger 75. Plate sleeve 86 is made of material that can support at least a minimum weight of the suspended personal radiation protection garment 20, shield 22, and flap 24. Plate sleeve 86 is operable for rotational motion of shoulder plate 84 relative to hanger 75. This allows operator 12 to freely move in the forward bending or rearward bending bodily motions. Bending forward will tilt shoulder plates 84 along with the tilt of the operator's shoulders, and the swivel motion of the sleeve on hanger 75 will allow hanger 75 to maintain a desirable vertical orientation rather than being forced into a tilted angulation, which would apply additional undesirable forces on hanger 75 and suspension device 60, as well as place additional downward force on cable 72.

In one embodiment, hanger 75 includes widget 76, cross bar 78, drop rod 80, and nut 82. Widget 76 can be a hook attached to cable 72, such that cable hook attaches to cross bar 78. Drop rod 80 can be positioned inside plate sleeve 86, such that plate sleeve 86 is welded on shoulder plate 84. Garment 20 can be placed over shoulder plates, such that garment 20 is suspended by hanger 75. Details relating to this hanger 75 embodiment are explained below in FIG. 4A and FIG. 4B.

In another embodiment, hanger 75 includes widget 76 and drop rod 80. Widget 76 can be a pulley attached to cable 72, such that pulley 76 attaches to hanger 75. Hanger 75 can be positioned inside plate sleeve 86, such that plate sleeve 86 is welded on shoulder plate 84. Garment 20 can be placed over shoulder plates 84, such that garment 20 is suspended by hanger 75. Details relating to this hanger 75 embodiment are explained below in FIG. 5.

In another embodiment, hanger 75 can be a unified, rigid piece, such that shoulder plate 84, plate sleeves 86, hanger 75, garment 20, shield 22, and flap 24 are integrated.

Suspended personal radiation protection face shield 22 may contain radiation-absorbing materials, such that face shield 22 attenuates X-rays, but is transparent to visible light allowing operator unhindered vision. Suspended personal radiation protection face shield 22 can be heavier and curve or bend around to cover more of operator's face than traditional radiation protection face shields 22, because operator 12 does not support the weight of the suspended personal radiation protection face shield 22. The suspended personal radiation protection face shield 22 protects operator 12 from radiation 18 approaching from the sides of operator's face. The operator 12 can wear normal corrective optical lenses behind face shield. Suspended personal radiation protection face shield 22 suspends from hanger 75. Suspended personal radiation protection face shield 22 allows operator 12 to move freely in the X, Y, and Z planes simultaneously, such that operator 12 can move normally as if operator 12 is not wearing a heavy radiation protection face shield 22.

Face shield support cables 88 are operable to suspend face shield 22 from hanger 75, such that operator 12 does not bear the weight of face shield 22. Face shield support cables 88 can also be ropes, wires, straps, rigid rods, or any suitable material to suspend the weight of face shield 22 and flap 24. Face shield support cables 88 can be affixed to hanger 75 in one or more places to achieve proper suspension. Face shield support cables 88 can be adjusted, such that face shield 22 and flap 24 are fitted properly to operator 12.

Suspended personal radiation protection flap 24 may contain radiation-absorbing materials, such as acrylic lead or other metals. Suspended personal radiation protection flap 24 can be thicker and heavier than traditional radiation protection flaps, because operator 12 does not support the weight of the suspended personal radiation protection flap 24. Additionally, suspended personal radiation protection flap 24 can cover more of operator's neck and thyroid area. Suspended personal radiation protection flap 24 suspends from shield 22, which suspends from hanger 75. Flap 24 can be suspended from hanger 75 as well as face shield 22. Suspended personal radiation protection flap 24 allows operator 12 to move freely in the X, Y, and Z planes simultaneously, such that operator 12 can move normally as if operator 12 is not wearing a heavy radiation protection flap 24.

In another embodiment, suspended personal radiation protection shield 22 and flap 24 can be integrated, such that one piece is formed. In another embodiment, suspended personal radiation protection garment 20, shield 22, and flap 24 can be integrated, such that one piece is formed. In another embodiment, suspended personal radiation protection garment 20, shield 22, and flap 24 can be integrated with hanger 75, such that one piece is formed.

Figure 3:
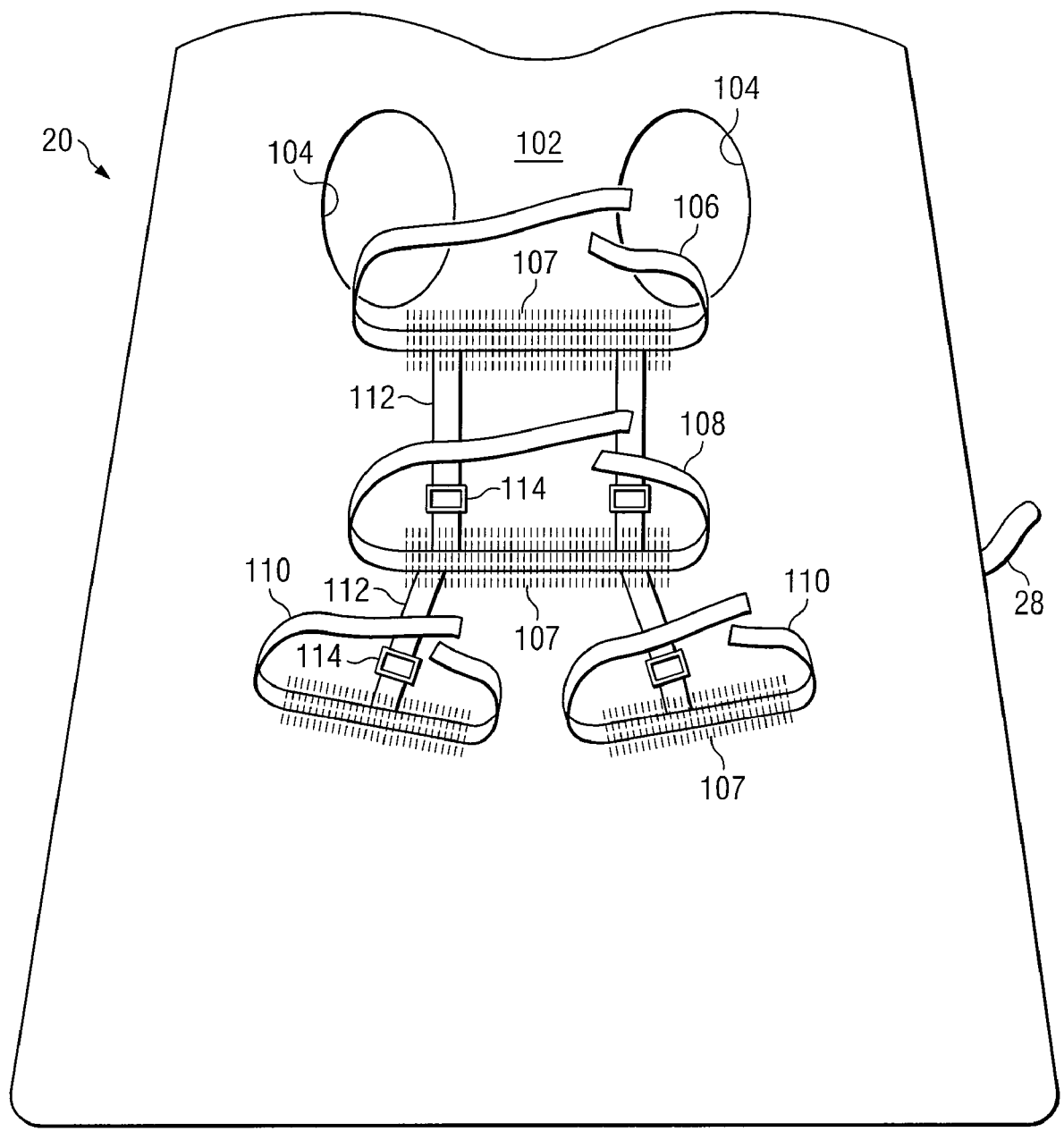
FIG. 3 is a simplified block diagram that illustrates a harness integrated with a personal radiation protective garment in accordance with a particular embodiment of the present invention.

FIG. 3 is a simplified block diagram that illustrates a harness integrated with personal radiation protective garment 20 in accordance with an embodiment of the present invention. Garment 20 includes an integrated harness, shoulder reinforcement 102, arm holes 104, and belt 28. Harness includes reinforced stitching 107, chest strap 106, waist strap 108, thigh strap 110, length adjusting strap 112, and length adjusting buckle 114.

The suspension force of suspension device 60 can be adjusted to be greater than the weight of the protective garment 20, shield 22, and flap 24, such that suspension device 60 can support a portion or all of operator's body weight. This provides added relief of the burden on the operator's spine, hips, knees, and other support structures during long procedures. A specialized harness system is incorporated into garment 20 utilizing straps and pads around the chest, torso, or thighs. The harness is integrated into the garment 20 in such a way that the support system will result in reduction in weight of the not only the garment 20 upon the operator 12, but the harness also can support a portion or all of the operator's weight. The suspended garment 20 becomes part of the suspension system and reduces the weight of operator 12 to some degree. The operator 12 can freely move, such that a majority of operator's body weight is supported by suspension device 60. The harness system can include a rigid seat-like apparatus.

Suspended personal radiation protection garment 20 may contain radiation-absorbing materials, such as lead or other metals. Suspended personal radiation protection garment 20 can be thicker and heavier than traditional radiation protection garments, because operator 12 does not support the weight of the suspended personal radiation protection garment 20. Additionally, suspended personal radiation protection garment 20 can cover more of operator's body, such as operator's arms and legs. Suspended personal radiation protection garment 20 suspends from hanger 75, which suspends from suspension device 60. Suspended personal radiation protection garment 20 can substantially contour to operator's body while garment 20 suspends from hanger 75, such that hanger 75 supports the weight of garment 20. Suspended personal radiation protection garment 20 allows operator 12 to move freely in the X, Y, and Z planes simultaneously, such that operator 12 can move normally as if operator 12 is not wearing a heavy radiation protection garment 20. Suspended personal radiation protection garment 20 allows operator 12 to wear sterile gloves and gown in the usual manner.

Shoulder reinforcement 102 on garment 20 provides an even distribution of force along the width of garment 20, such that garment 20 is not distorted while suspended on shoulder plate 84. Shoulder reinforcement 102 can include extra material, reinforcement stitching, or any means suitable to even distribution of force along the width of garment 20.

Arm holes 104 are provided for operator 12 to freely move around arms and hands. Arm holes 104 can include sleeves 32 to provide more protection to operator's arms.

Belt 28 on garment 20 can include Velcro, buckle, or fastening means, such that belt 20 helps garment stay closed. Belt 28 can be fastened on front, side, or rear of garment. Belt 28 also helps suspended personal radiation protection garment 20 substantially contour to operator's body, such that operator's body is properly protected.

Harness chest strap 106 wraps around operator's chest to help secure operator's body. The suspension device 60 can suspend garment 20 and harness, such that suspension device 60 supports a portion or all of operator's weight. The effect of suspending operator 12 allows operator 12 to freely move with reduced weight, such that a majority of operator's body weight is supported by suspension device 60. This provides added relief of the burden on the operator's spine, hips, knees, and other support structures during long procedures. Chest strap 106 can include Velcro, buckle, or fastening means, such that chest strap 106 is secure around operator's chest.

Harness waist strap 108 wraps around operator's waist to help secure operator's body. The suspension device 60 can suspend garment 20 and harness, such that suspension device 60 supports a portion or all of operator's weight. The effect of suspending operator 12 allows operator 12 to move about freely move with reduced weight, such that a majority of operator's body weight is supported by suspension device 60. This provides added relief of the burden on the operator's spine, hips, knees, and other support structures during long procedures. Waist strap 108 can include Velcro, buckle, or fastening means, such that waist strap 108 is secure around operator's waist.

Harness thigh strap 110 wraps around operator's thighs to help secure operator's body. The suspension device 60 can suspend garment 20 and harness, such that suspension device supports a portion or all of operator's weight. The effect of suspending operator 12 allows operator 12 to move about freely with reduced weight, such that a majority of operator's body weight is supported by suspension device 60. This provides added relief of the burden on the operator's spine, hips, knees, and other support structures during long procedures. Thigh straps 110 can include Velcro, buckle, or fastening means, such that thigh straps 110 are secure around operator's thigh.

Length adjusting straps 112 allow operator to customize harness to operator's height. Length adjusting straps 112 can be secured and adjusted by length adjusting buckle 114.

Reinforced stitching 107 allows harness to be integrated with garment 20. Reinforced stitching is used on garment 20, chest strap 106, waist strap 108, and thigh straps 110. Reinforced stitching material 107 can support operator's weight.

In another embodiment of this invention, the harness system will not be associated with radiation protection garment 20, and harness can be used to support a portion or all of the operator's body weight for the performance of medical or surgical procedures that do not require radiation. This prevents fatigue of operator due to standing in proper position for prolonged periods.

Figure 4A:
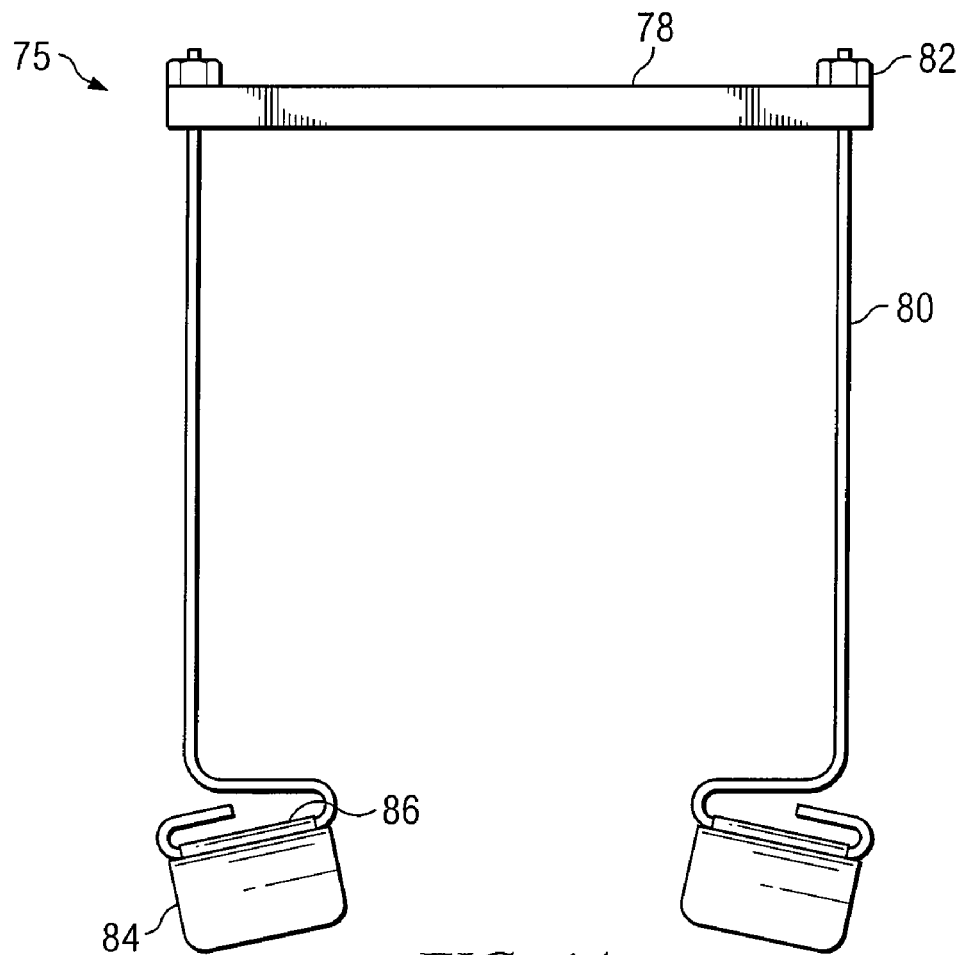
FIGS. 4A and 4B are simplified block diagrams that illustrate a hanger attached to a shoulder plate via a plate sleeve in accordance with an embodiment of the present invention.
Figure 4B:
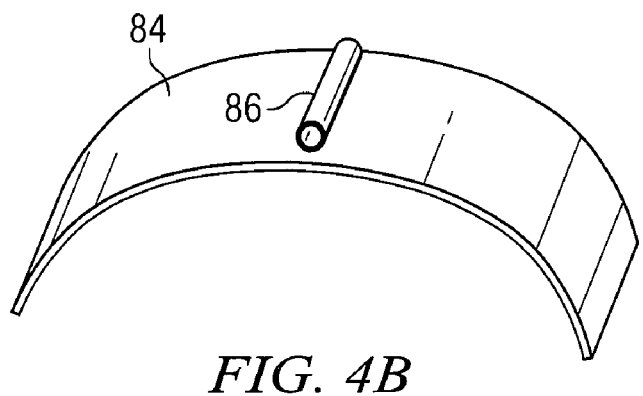

FIGS. 4A and 4B are a simplified block diagram that illustrate a hanger 75 attached to shoulder plate 84 via plate sleeve 86 in accordance with an embodiment of the present invention. Hanger 75 includes cross bar 78, drop rod 80, and nut 82.

Cross bar 78 attaches to cable via widget. Cross bar is made of material that can support at least a minimum weight of the suspended personal radiation protection garment 20, shield 22, and flap 24. Cross bar 78 is positioned above operator's head to avoid collision with operator's head during manipulations. Cross bar 78 can include grooves where widget attaches, such that weight is properly distributed when operator 12 leans forward or backward.

Drop rod 80 attaches to cross bar 78 and is held in place with a nut 82. Drop rod 80 is made of material that can support at least a minimum weight of the suspended personal radiation protection garment 20, shield 22, and flap 24. Drop rod 80 can attach to shoulder plate 84 in various embodiments. In one embodiment, drop rod 80 can be angled inward, such that drop rod 80 is inserted into shoulder plate sleeve 86 closer to operator's neck. This particular embodiment is effective at distributing weight and supporting the suspended garment 20, shield 22, and flap 24.

Shoulder plate 84 is suspended by hanger 75. Shoulder plate 84 is made of material that can support at least a minimum weight of the suspended personal radiation protection garment 20, shield 22, and flap 24. Shoulder plate 84 can be one piece that extends over both shoulders or shoulder plate 84 can be two pieces, such that each shoulder plate 84 is positioned over operator's shoulders. Suspended personal radiation protection garment 20 can be placed on shoulder plate 84, such that shoulder plate 84 supports the weight of garment 20. Shoulder plates 84 can be positioned slightly above operator's shoulders, such that shoulder plates 84 are a substitute for operator's shoulders, while garment 20 is still substantially contoured to operator's body.

Plate sleeve 86 can be welded on shoulder plate 84. Plate sleeve 86 is operable for hanger 75 to be inserted, such that plate sleeve 86 securely attaches shoulder plate 84 to hanger 75. Plate sleeve 86 is operable for rotational motion of shoulder plate 84 relative to hanger 75. This allows operator 12 to freely move in the forward bending or rearward bending bodily motions. Bending forward will tilt shoulder plates 84 along with the tilt of the operator's shoulders, and the swivel motion of the sleeve on hanger 75 will allow hanger 75 to maintain a desirable vertical orientation rather than being forced into a tilted angulation, which would apply additional undesirable forces on hanger 75 and suspension device 60, as well as place additional downward force on cable 72. In another embodiment, plate sleeve can be fixed. Plate sleeve 86 is made of material that can support at least a minimum weight of the suspended personal radiation protection garment 20, shield 22, and flap 24.

Figure 5:
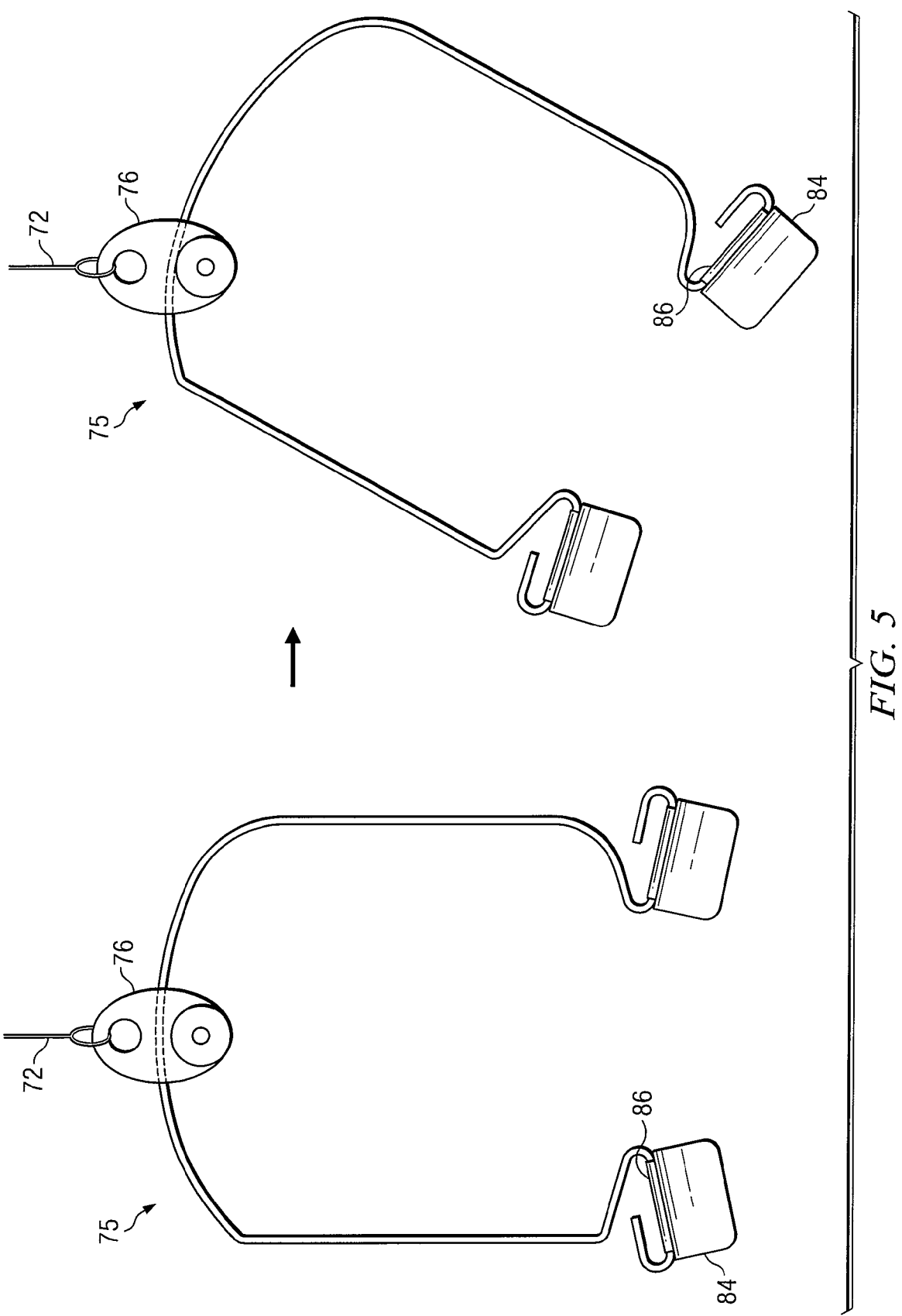
FIG. 5 is a simplified block diagram that illustrates a hanger with a sideways bending modification in accordance with an embodiment of the present invention.

FIG. 5 is a simplified block diagram that illustrates a hanger 75 with a sideways bending modification in accordance with an embodiment of the present invention. Hanger 75 suspends from pulley 76, which suspends from cable 72. Shoulder plate 84 with integrated plate sleeve 86 suspend from hanger 75.

Cable 72 is suspended from balancer 70 and attaches to pulley 76. In other embodiments, cable 72 may also include a rope or a belt. Cable 72 is several feet long and allows operator 12 to move extensively in the vertical Z-axis. Cable 72 also allows operator to freely move slightly outside the perimeter of the plane formed by the X and Y axes. Cable 72 can include a swivel mount that permits free rotation of the cable suspension mechanism allowing operator 12 to twist as needed. This may include a swivel hook or snap that connects the cable 72 to hanger 75. Cable 72 is operable to safely hold the amount of weight and force caused by the suspended personal radiation protection garment 20, shield 22, and flap 24.

Pulley 76 is operable to roll along hanger 75, such that pulley 76 rolls along hanger 75 when operator 12 bends sideways. Pulley 76 attaches to cable 72 and hanger 75. Pulley 76 is made of material to support weight of suspended personal radiation protection garment 20, shield 22, and flap 24. For example, when operator 12 bends sideways, pulley 76 will roll along hanger 75, such that hanger 75 becomes tilted. This effect allows operator 12 to freely bend sideways, such that suspended personal radiation protection garment 20, shield 22, and flap 24 are all properly suspended.

Hanger 75 is operable to suspend the personal radiation protection garment 20, shield 22, and flap 24. Hanger 75 can be attached to pulley 76, such that pulley 76 allows hanger 75 to tilt when operator 12 bend sideways. Hanger 75 can be positioned above operator's head to avoid collision with operator's head during manipulations. Personal radiation protection garment 20, shield 22, and flap 24 can be detached to hanger 75, attached to hanger 75, and remain attached to hanger 75 indefinitely. For example, garment 20 can rest on hanger 75 similar to a clothes hanger, such that garment 20 is not resting on operator's body. FIG. 5 illustrates two different embodiments for the design of hanger 75. Hanger 75 can also include a component operable to prevent pulley 76 from moving beyond the hanger's edge.

Shoulder plate 84 is suspended by hanger 75. Shoulder plate 84 is made of material that can support at least a minimum weight of the suspended personal radiation protection garment 20, shield 22, and flap 24. Shoulder plate 84 can be one piece that extends over both shoulders or shoulder plate can be two pieces, such that each shoulder plate 84 is positioned over operator's shoulders. Suspended personal radiation protection garment 20 can be placed on shoulder plate 84, such that shoulder plate 84 supports the weight of the garment 20. Shoulder plates 84 can be positioned slightly above operator's shoulders, such that shoulder plates 84 are a substitute for operator's shoulders while garment 20 is still substantially contoured to operator's body.

Plate sleeve 86 can be welded on shoulder plate 84. Plate sleeve 86 is operable for hanger 75 to be inserted, such that plate sleeve 86 securely attaches shoulder plate 84 to hanger 75. Plate sleeve 86 is made of material that can support at least a minimum weight of the suspended personal radiation protection garment 20, shield 22, and flap 24.

Figure 6:
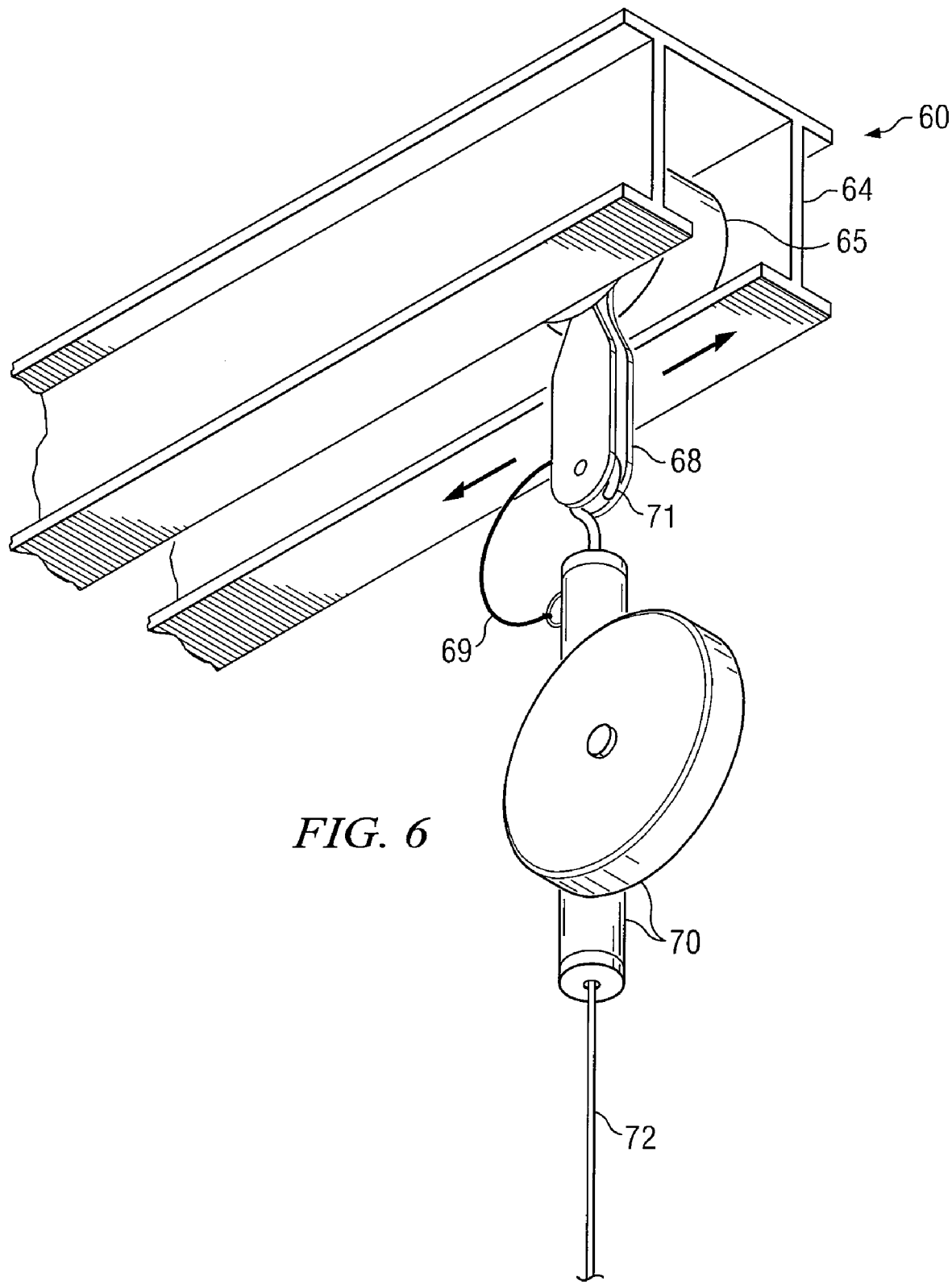
FIG. 6 is a simplified block diagram that illustrates a trolley and balancer in accordance with an embodiment of the present invention.

FIG. 6 is a simplified block diagram that illustrates a trolley 68 and a balancer 70 in accordance with an embodiment of the present invention. Suspension device 60 includes bridge 64, roller 65, trolley 68, safety cable 69, balancer 70, hook 71, and cable 72.

Bridge 64 can be positioned perpendicular between rails 62 over the area of operator's workplace. Bridge 64 represents the length of the Y-axis that operator can move freely within while wearing the suspended personal radiation protection garment 20, shield 22, and flap 24. Bridge 64 is affixed to rails 62 and movable along rails by an end truck 66 on each rail 62. Bridge 64 can include a runway. Details of bridge 64 interacting with other components are explained above in FIG. 1.

Roller 65 attaches to trolley 64 and is positioned in bridge runway, such that roller 65 can slide along bridge runway. Roller 65 is operable to easily slide along bridge runway, such that operator 12 can move freely.

Trolley 68 is positioned in bridge runway. Trolley 68 is freely movable along the Y-axis of bridge 64. The length of the Y-axis spatial movement of trolley 68 can be limited to the ends of bridge runway, such that end trucks 66 prevent further movement. Trolley 68 can include a latch for balancer 70 attachment and a safety cable 69. For extra safety, safety cable 69 or chain may be attached to a separate trolley, which is allowed to move adjacent to weight bearing trolley 68. Trolley 68 can support the weight for suspended personal radiation protection garment 20, shield 22, and flap 24, such that operator 12 can move freely in the X and Y spatial planes defined above by the length of the rails 66 and the length of the bridge 64. The plane defined by the X and Y spatial axes is designed to correspond to operator's desired work area on the floor. Operator 12 wearing suspended personal radiation protection garment 20, shield 22, and flap 24 has very smooth and facile motion within this plane. In another embodiment of this invention, a telescoping component on bridge 64 can allow extension of trolley 68 farther than the length of the bridge 64, such that the Y spatial axis is greater for operator to freely move within the X, Y plane.

Safety cable 69 can be permanently affixed to trolley 68 and balancer 70. Safety cable 69 is operable to suspend the weight of balancer 70, hanger 75, garment 20, shield 22, and flap 24, such that operator 12 is protected if balancer 70 becomes detached from trolley 68. For extra safety, safety cable 69 or chain may be attached to a separate trolley, which is allowed to move adjacent to weight bearing trolley 68.

Balancer 70 can be a spring balancer 70 attached to trolley 68 by a hook 71, and a safety chain 69 or cable for the event of hook failure. Spring balancer 70 applies constant and controllable uplifting force on garment 20, shield 22, and flap 24. Spring balancer 70 can include a coiled flat spring, similar to a clock spring, attached to a reel with a conical shape. The conical shape provides a variable mechanical advantage, which offsets the variance of the force provided by the spring as it winds or unwinds, such that there is a relatively constant force on cable within a definable working range. Spring balancer 70 allows operator 12 wearing suspended personal radiation protection garment 20, shield 22, and flap 24 freedom of motion in the vertical Z-axis spatial plane. Operator 12 wearing the heavy and bulky garment 20, shield 22, and flap 24 can freely perform vertical motion activities, such as stooping, leaning, squatting, standing on an elevated surface. The tension can be designed to provide optimum relief of garment's 20 weight for operator 12, and this force can be constant in all positions by operator 12. Spring balancer 70 applies a constant force to oppose the weight regardless of how much cable is extended. Balancer 70 can also take on the different embodiments explained above in FIG. 1.

Hook 71 is affixed to balancer 70 and is a means to suspend balancer 70 from trolley 68. Hook 71 is made of material that can support a minimum weight of balancer 70, hanger 75, operator 12, garment 20, shield 22, and flap 24. If hook 71 fails, then safety cable 69 can prevent damage to operator 12.

Cable 72 is suspended from balancer 70 and attaches to hanger 75. In other embodiments, cable 72 may also include a rope or a belt. Cable 72 is several feet long and allows operator 12 to move extensively in the vertical Z-axis. Cable 72 also allows operator to freely move slightly outside the perimeter of the plane formed by the X and Y axes. Cable 72 can include a swivel mount that permits free rotation of the cable suspension mechanism allowing operator 12 to twist as needed. This may include a swivel hook or snap that connects the cable 72 to hanger 75. Cable 72 is operable to safely hold the amount of weight and force caused by the suspended personal radiation protection garment 20, shield 22, and flap 24.

Figure 7:
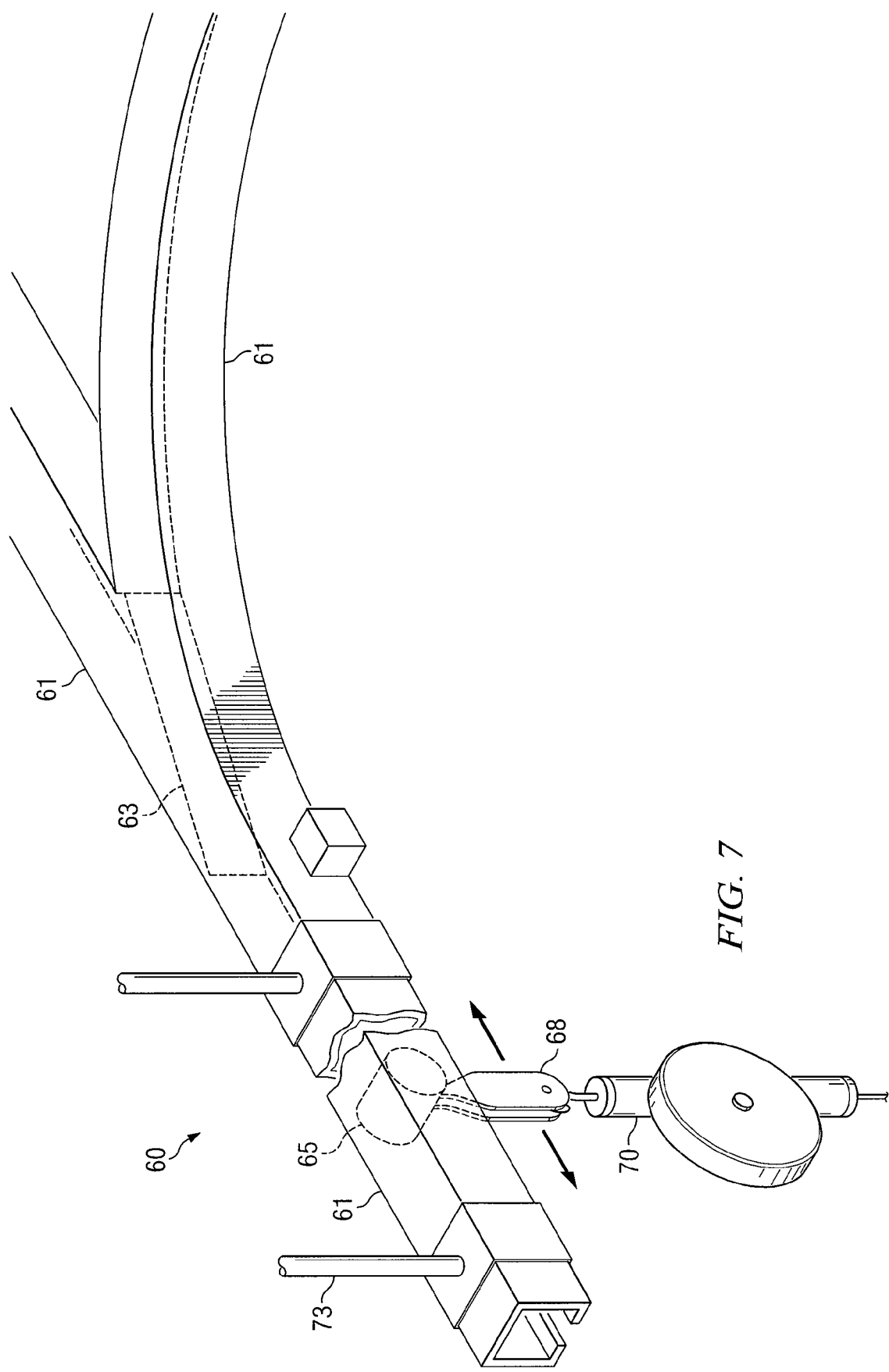
FIG. 7 is a simplified block diagram that illustrates a monorail in accordance with an embodiment of the present invention.

FIG. 7 is a simplified block diagram that illustrates a monorail 61 track in accordance with an embodiment of the present invention. A monorail 61 track can be used in place of parallel rail system described above in FIG. 1. Monorail 61 track includes monorail 61, switch 63, roller 65, trolley 68, balancer 70, and ceiling mounts 73.

Monorail 61 can be ceiling mounted in the orientation that best fits the particular room and type of operation. Trolley 68 can run freely along the monorail 61 with balancer 70 and garment 20 suspended from trolley 68. Monorail 61 can include curves, and extra tracks connected and controlled by switches 63. Monorail 61 has the advantage of being less expensive, easier to install, and potentially installable in operating rooms that may not accommodate the parallel rail track due to its dimensions. Operator 12 can move freely along the path of monorail 61, but operator 12 would be more limited in the motion away from the monorail 61 in a perpendicular direction. Some motion in this direction would be allowed by the spring balancer 70, which could reel out several feet of cable 72 accordingly. However, balancer 70 would exert some pull forces on the operator 12, which hinder motion somewhat. to operator's body. Monorail 61 can include a runway, such that trolley 68 can move along monorail 61.

Switches 63 are integrated with monorail 61. Switches 63 are operable to connect different tracks of monorail 61, such that operator 12 can move to other areas of the room. Operator 12 can operate switches by an electronic device or any suitable means.

Roller 65 attaches to trolley 68 and is positioned in monorail runway, such that roller 65 can slide along monorail runway. Roller 65 is operable to easily slide along monorail runway, such that operator 12 can move freely.

Trolley 68 is positioned in monorail runway. Trolley 68 is freely movable along monorail 61. Trolley 68 can support the weight for suspended personal radiation protection garment 20, shield 22, and flap 24. Operator 12 wearing suspended personal radiation protection garment 20, shield 22, and flap 24 has very smooth and facile motion along monorail 61 path. In another embodiment of this invention, a telescoping component on monorail 61 can allow extension of trolley 68 farther out than monorail 61 path.

Balancer 70 can be a spring balancer 70 attached to trolley by a hook, and a safety chain or cable for the event of hook failure. Spring balancer 70 applies constant and controllable uplifting force on garment 20, shield 22, and flap 24. Spring balancer 70 can include a coiled flat spring, similar to a clock spring, attached to a reel with a conical shape. The conical shape provides a variable mechanical advantage, which offsets the variance of the force provided by the spring as it winds or unwinds, such that there is a relatively constant force on cable within a definable working range. Spring balancer 70 allows operator 12 wearing suspended personal radiation protection garment 20, shield 22, and flap 24 freedom of motion in the vertical Z-axis spatial plane. Operator 12 wearing the heavy and bulky garment 20, shield 22, and flap 24 can freely perform vertical motion activities, such as stooping, leaning, squatting, standing on an elevated surface. The tension can be designed to provide optimum relief of garment's weight for operator 12, and this force can be constant in all positions by operator 12. Spring balancer 70 applies a constant force to oppose the weight regardless of how much cable 72 is extended. Balancer can also take on the different embodiments explained above in FIG. 1.

Ceiling mounts 73 are affixed to ceiling and attached to monorail 61. Ceiling mounts 73 are operable to securely fasten monorail 61, such that ceiling mounts 73 can support a minimum weight of monorail track 61, trolley 68, balancer 70, hanger 75, operator 12, garment 20, shield 22, and flap 24.

Figure 8:
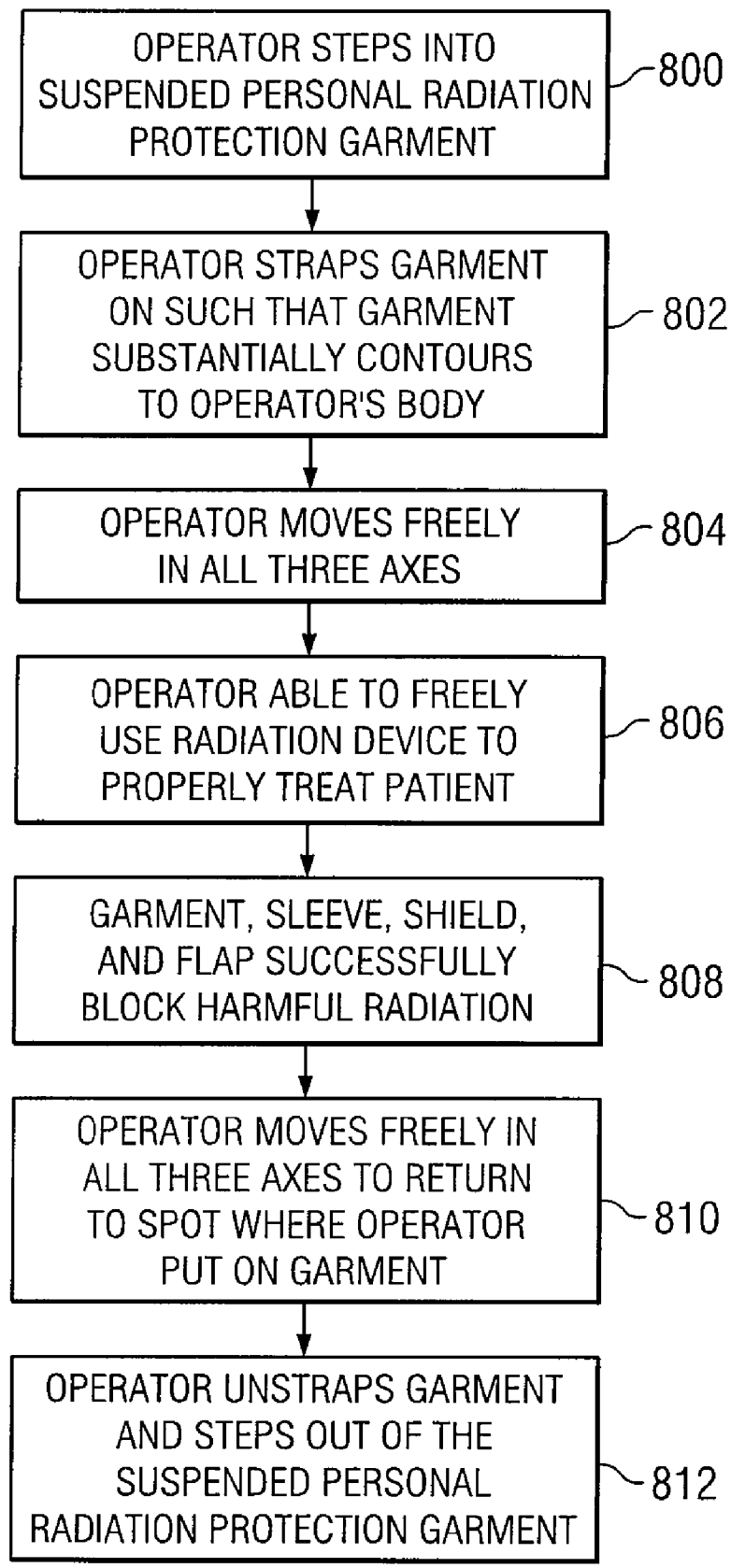
FIG. 8 is a simplified flowchart that illustrates an example method of the suspended personal radiation protection system in accordance with an embodiment of the present invention.

FIG. 8 is a simplified flowchart that illustrates an example method of the suspended personal radiation protection system in accordance with an embodiment of the present invention. The flowchart begins at step 800, where operator 12 steps into suspended personal radiation protection garment 20, shield 22, and flap 24. Operator 12 can adjust suspension device's 60 height, such that shoulder plates 20 are suspended slightly above operator's shoulders. Operator 12 can adjust the length of garment 20 by fastening means, such that garment 20 covers substantially all of operator's legs. Suspended garment 20, shield 22, and flap 24 are weightless to operator 12.

At step 802, operator 12 or another individual can strap garment 20 closed by fastening means 26, such that garment 20, shield 22, and flap 24 are substantially contoured to operator's body. Operator 12 can fasten belt 28 around garment 20, such that garment 20 is secured even further. Operator 12 can also wear sterile gown and gloves. This process is very fast and effortless.

At step 804, operator 12 can move freely in all three spatial planes while wearing suspended personal radiation protection garment 20, shield 22, and flap 24. Operator 12 can walk diagonally, crouch, or bend sideways in a free motion while receiving protection of suspended personal radiation protection garment 20, shield 22, and flap 24.

At step 806, operator 12 has complete freedom of motion to use radiation device to properly treat patient 14. Suspended personal radiation protection garment 20, shield 22, and flap 24 are substantially weightless to operator 12, such that operator 12 is comfortable and unhindered. Operator's arms are able to freely move in order to properly treat patient 14. Operator 12 can bend over patient 14 without causing pain to operator's spine.

At step 808, suspended garment 20, shield 22, and flap 24 properly protect operator 12 from harmful radiation 18. Since garment 20 is suspended, garment 20, shield 22, and flap 24 can be heavier to provide more protection to operator 12. Suspended garment 20, shield 22, and flap 24 are substantially contoured to operator's body, such that a substantial area of operator's body is protected. Suspended garment 20 can also be made of thicker material to provide extra protection to operator 12. Sleeve 32 on garment 20 can provide further protection to arms and armpit area.

At step 810, operator 12 can move freely to return to spot where operator 12 initially stepped into suspended personal radiation protection garment 20, shield 22, and flap 24. Operator 12 can move freely in all three spatial planes while wearing suspended personal radiation protection garment 20, shield 22, and flap 24. Operator 12 can walk diagonally, crouch, or bend sideways in a free motion while receiving protection of suspended personal radiation protection garment 20, shield 22, and flap 24.

At step 812, operator 12 or another individual can quickly and effortlessly unfasten garment 20 and belt 28. Operator 12 can easily step out from the suspended garment 20, shield 22, and flap 24. garment 20, shield 22, and flap 24 can remain suspended.

It is important to note that the stages and steps described above illustrate only some of the possible scenarios that may be executed by, or within, the present system. Some of these stages and/or steps may be deleted or removed where appropriate, or these stages and/or steps may be modified, enhanced, or changed considerably without departing from the scope of the present invention. In addition, a number of these operations have been described as being executed concurrently with, or in parallel to, one or more additional operations. However, the timing of these operations may be altered. The preceding example flows have been offered for purposes of teaching and discussion. Substantial flexibility is provided by the tendered system in that any suitable arrangements, chronologies, configurations, and timing mechanisms may be provided without departing from the broad scope of the present invention. Accordingly, any appropriate structure, component, or device may be included within suspended personal radiation protection system 10 to effectuate the tasks and operations of the elements and activities associated with executing compatibility functions.

Figure 9:
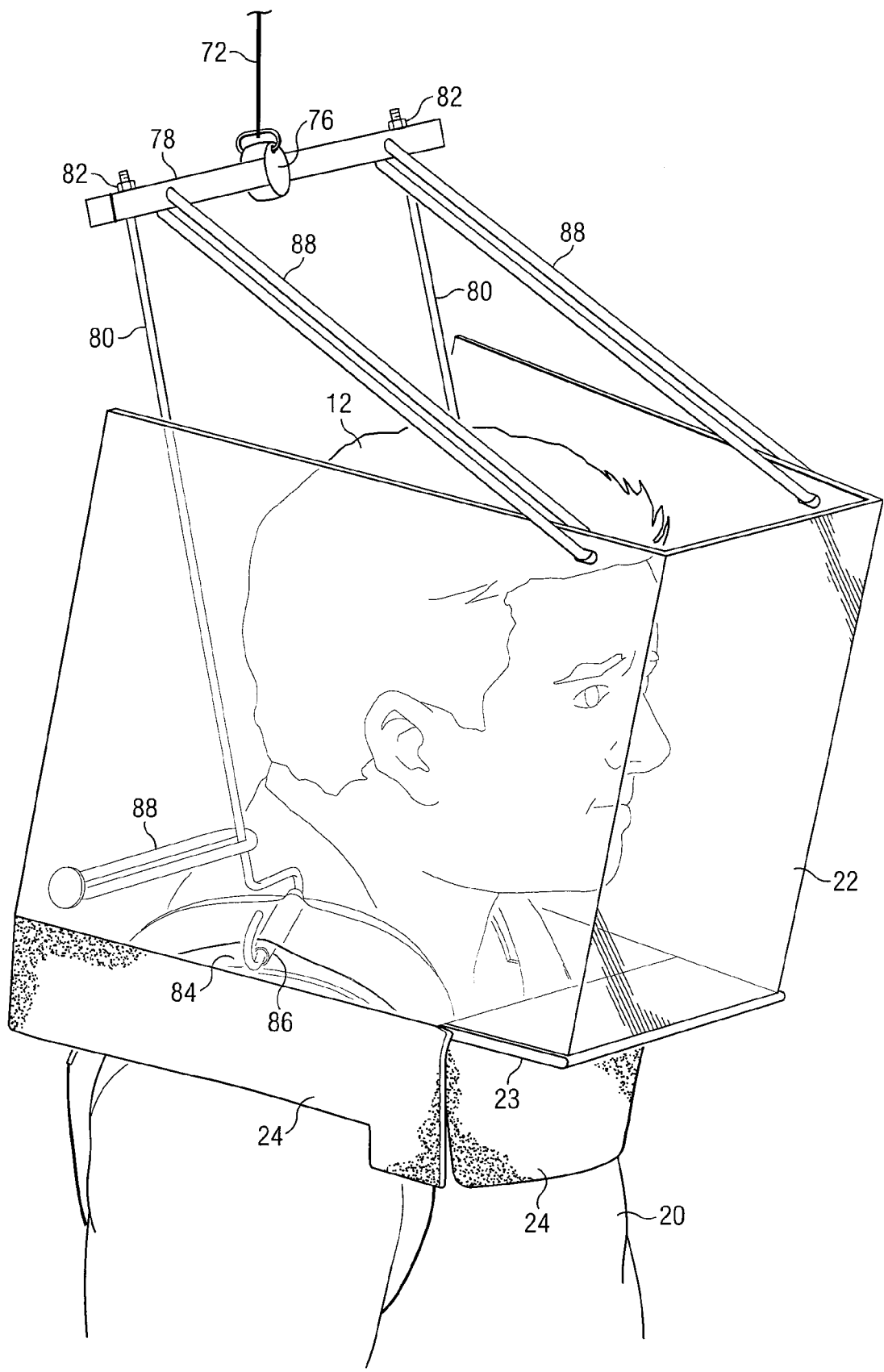
FIG. 9 is a simplified block diagram that illustrates a face shield and flap in accordance with an embodiment of the present invention.

FIG. 9 is a simplified block diagram that illustrates a face shield and flap suspending from hanger in accordance with an embodiment of the present invention. Hanger includes widget 76, cross bar 78, drop rod 80, nut 82, shoulder plate 84, plate sleeve 86, and shield support cables 88.

Hanger 75 is operable to suspend the personal radiation protection garment 20, shield 22, and flap 24. Hanger 75 is attached to cable 72. Hanger 75 is positioned above operator's head to avoid collision with operator's head during manipulations. Personal radiation protection garment 20, shield 22, and flap 24 can be detached to hanger 75, attached to hanger 75, and remain attached to hanger 75 indefinitely. For example, garment 20 can rest on the hanger similar to a clothes hanger, such that garment 20 is not resting on operator's body. Shield 22 and flap 24 can be suspended from hanger 75 by ropes, wires, cables or any other suitable means.

Widget 76 connects hanger to cable. Widget 76 can be a hook, a pulley, or any suitable means to attach hanger 75 to cable 72. Widget 76 is made of material that can support a minimum weight of the suspended personal radiation protection garment 20, shield 22, and flap 24. Pulley widget 76 allows operator 12 to bend sideways, such that pulley widget 76 moves along hanger 75 to properly distribute weight. Details relating to pulley widget 76 are explained below in FIG. 5.

Cross bar 78 attaches to cable 72 via widget 76. Cross bar 78 is made of material that can support at least a minimum weight of the suspended personal radiation protection garment 20, shield 22, and flap 24. Cross bar 78 is positioned above operator's head to avoid collision with operator's head during manipulations. Cross bar 78 can include grooves where widget 76 attaches, such that weight is properly distributed when operator 12 leans forward or backward.

Drop rod 80 attaches to cross bar 78 and is held in place with a nut 82. Drop rod 80 is made of material that can support at least a minimum weight of the suspended personal radiation protection garment 20, shield 22, and flap 24. Drop rod 80 can attach to shoulder plate 84 in various embodiments. In one embodiment, drop rod 80 can be angled inward, such that drop rod 80 is inserted into shoulder plate sleeve 84 closer to operator's neck. This particular embodiment is effective at distributing weight and supporting the suspended garment 20, shield 22, and flap 24.

Shoulder plate 84 is suspended by hanger 75. Shoulder plate 84 is made of material that can support at least a minimum weight of the suspended personal radiation protection garment 20, shield 22, and flap 24. Shoulder plate 84 can be one piece that extends over both shoulders or shoulder plate 84 can be two pieces, such that each shoulder plate 84 is positioned over operator's shoulders. Suspended personal radiation protection garment 20 can be placed on shoulder plate 84, such that shoulder plate 84 supports the weight of garment 20. Shoulder plates 84 can be positioned slightly above operator's shoulders, such that shoulder plates 84 act as a substitute for operator's shoulders while the garment 20 is still substantially contoured to operator's body.

Plate sleeve 86 can be welded or affixed to shoulder plate 84. Plate sleeve 86 is operable for hanger to be inserted, such that plate sleeve 86 securely attaches shoulder plate 84 to hanger 75. Plate sleeve 86 is made of material that can support at least a minimum weight of the suspended personal radiation protection garment 20, shield 22, and flap 24. Plate sleeve 86 is operable for rotational motion of shoulder plate 84 relative to hanger 75. This allows operator 12 to freely move in the forward bending or rearward bending bodily motions. Bending forward will tilt shoulder plates 84 along with the tilt of the operator's shoulders, and the swivel motion of the sleeve on hanger 75 will allow hanger 75 to maintain a desirable vertical orientation rather than being forced into a tilted angulation, which would apply additional undesirable forces on hanger 75 and suspension device 60, as well as place additional downward force on cable 72.

Suspended personal radiation protection face shield 22 may contain radiation-absorbing materials, such that face shield 22 attenuates X-rays, but is transparent to visible light allowing operator unhindered vision. Suspended personal radiation protection face shield 22 can be heavier and curve or bend around to cover more of operator's face than traditional radiation protection face shields 22, because operator 12 does not support the weight of the suspended personal radiation protection face shield 22. The suspended personal radiation protection face shield 22 protects operator 12 from radiation 18 approaching from the sides of operator's face. The operator 12 can wear normal corrective optical lenses behind face shield. Suspended personal radiation protection face shield 22 suspends from hanger 75. Suspended personal radiation protection face shield 22 allows operator 12 to move freely in the X, Y, and Z planes simultaneously, such that operator 12 can move normally as if operator 12 is not wearing a heavy radiation protection face shield 22.

Face shield support cables 88 are operable to suspend face shield 22 from hanger 75, such that operator 12 does not bear the weight of face shield 22. Face shield support cables 88 can also be ropes, wires, straps, rigid rods, or any suitable material to suspend the weight of face shield 22 and flap 24. Face shield support cables 88 can be affixed to hanger 75 in one or more places to achieve proper suspension. Face shield support cables 88 can be adjusted, such that face shield 22 and flap 24 are fitted properly to operator 12.

Floor plate 23 can be integrated with shield 24, such that floor plate 23 may contain radiation-absorbing materials, such as acrylic lead or other metals. Floor plate 23 can be a thicker material than flap, such that floor plate 23 protects operator from harmful radiation.

Suspended personal radiation protection flap 24 may contain radiation-absorbing materials, such as acrylic lead or other metals. Flap can be a softer fabric containing radiation-absorbing materials. Suspended personal radiation protection flap 24 can be thicker and heavier than traditional radiation protection flaps, because operator 12 does not support the weight of the suspended personal radiation protection flap 24. Additionally, suspended personal radiation protection flap 24 can cover more of operator's neck and thyroid area. Suspended personal radiation protection flap 24 suspends from shield 22, which suspends from hanger 75. Flap 24 can be suspended from hanger 75 as well as face shield 22. Suspended personal radiation protection flap 24 allows operator 12 to move freely in the X, Y, and Z planes simultaneously, such that operator 12 can move normally as if operator 12 is not wearing a heavy radiation protection flap 24.

In another embodiment, suspended personal radiation protection shield 22 and flap 24 can be integrated, such that one piece is formed. In another embodiment, suspended personal radiation protection garment 20, shield 22, and flap 24 can be integrated, such that one piece is formed. In another embodiment, suspended personal radiation protection garment 20, shield 22, and flap 24 can be integrated with hanger 75, such that one piece is formed.

Although the present invention has been described in detail with reference to particular embodiments, it should be understood that various other changes, substitutions, and alterations may be made hereto without departing from the spirit and scope of the present invention. The illustrated suspension device 60 in FIG. 1 has only been offered for purposes of example and teaching. Suitable alternatives and substitutions are envisioned and contemplated by the present invention: such alternatives and substitutions being clearly within the broad scope of suspension device 60. Using analogous reasoning, the hanger 75 illustrated by FIG. 1 may be supplanted by a single piece hanger, wires, or any other suitable devices that are conducive to properly supporting the weight of the operator 12, garment 20, face shield 22, and flap 24. In addition, while the foregoing discussion has focused on medical procedures, any other suitable environment requiring radiation protection may benefit from the compatibility teachings provided herein. Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. A method, comprising:
providing a garment that substantially contours to an operator's body, but not the operator's head, to protect a portion of the operator's body from radiation, and wherein the garment is suspended from a suspension component, wherein the suspension component includes a bridge configured to ride along one or more rails, and the suspension component includes a trolley that rides along the bridge, and wherein the bridge is capable of providing a purely lateral axis of motion and the trolley is capable of providing a purely linear axis of motion, the garment being configured to secure a face shield thereon, the face shield protecting at least a portion of the operator's head from radiation.

2. The method of claim 1, wherein the suspension component allows the operator, who is wearing the garment to move freely in X, Y, and Z spatial planes simultaneously, and wherein the garment is substantially weightless to the operator.

3. The method of claim 1, wherein the suspension component is operable to support weight of the operator, and wherein the operator can move around with reduced weight.

4. The method of claim 1, wherein the face shield is substantially weightless to operator, and wherein the face shield is substantially transparent to visible light.

5. The method of claim 3, wherein the garment further comprises a flap, the flap being substantially weightless to the operator, and wherein the flap is operable to protect the operator from radiation between the garment and the face shield.

6. The method of claim 1, wherein the garment comprises a removable sleeve, wherein the sleeve is operable to protect the operator from radiation.

7. The method of claim 1, wherein the suspension component is mounted to a ceiling.

8. The method of claim 1, wherein the suspension component further comprises a constant force balancer, wherein the balancer is a selected one of a group of balancers, the group consisting of:
a) a spring balancer;
b) one or more counterweights;
c) a constant force spring;
d) a pneumatic balancer;
e) an air balancer;
f) a spring motor; and
g) an intelligent assist device.

9. A system, comprising:
providing a garment that substantially contours to an operator's body, but not the operator's head, to protect a portion of the operator's body from radiation, and wherein the garment is suspended from a suspension component, wherein the suspension component includes a bridge configured to ride along one or more rails, and the suspension component includes a trolley that rides along the bridge, and wherein the bridge is capable of providing a purely lateral axis of motion and the trolley is capable of providing a purely linear axis of motion, the garment being configured to secure a face shield thereon, the face shield protecting at least a portion of the operator's head from radiation.

10. The system of claim 9, wherein the suspension component allows the operator, who is wearing the garment to move freely in X, Y, and Z spatial planes simultaneously, and wherein the garment is substantially weightless to the operator.

11. The system of claim 9, wherein the suspension component is operable to support weight of the operator, and wherein the operator can move around with reduced weight.

12. The system of claim 9, wherein the face shield is substantially weightless to the operator, and wherein the face shield is substantially transparent to visible light.

13. The system of claim 12, wherein the garment further comprises a flap, the flap being substantially weightless to the operator, and wherein the flap is operable to protect the operator from radiation between the garment and the face shield.

14. The system of claim 9, wherein the garment comprises a removable sleeve, wherein the sleeve is operable to protect the operator from radiation.

15. The system of claim 9, wherein the suspension component is mounted to a ceiling.

16. The system of claim 9, wherein the suspension component further comprises a constant force balancer, wherein the balancer is a selected one of a group of balancers, the group consisting of:

a) a spring balancer;
b) one or more counterweights;
c) a constant force spring;
d) a pneumatic balancer;
e) an air balancer;
f) a spring motor; and
g) an intelligent assist device.

17. An apparatus, comprising:
a garment that substantially contours to an operator's body, but not the operator's head, to protect a portion of the operator's body from radiation, and wherein the garment is suspended from a suspension component, wherein the suspension component includes a bridge configured to ride along one or more rails, and the suspension component includes a trolley that rides along the bridge, and wherein the bridge is capable of providing a purely lateral axis of motion and the trolley is capable of providing a purely linear axis of motion, the garment being configured to secure a face shield thereon, the face shield protecting at least a portion of the operator's head from radiation.

18. The apparatus of claim 17, wherein the suspension component allows the operator, who is wearing the garment to move freely in X, Y, and Z spatial planes simultaneously, and wherein the garment is substantially weightless to the operator.

19. The apparatus of claim 17, wherein the suspension component is operable to support weight of the operator, and wherein the operator can move around with reduced weight.

20. The apparatus of claim 17, wherein the face shield is substantially weightless to the operator, and wherein the face shield is substantially transparent to visible light.

21. The apparatus of claim 20, wherein the garment further comprises a flap, the flap being substantially weightless to the operator, and wherein the flap is operable to protect the operator from radiation between the garment and the face shield.

22. The apparatus of claim 17, wherein the garment comprises a removable sleeve, wherein the sleeve is operable to protect the operator from radiation.

23. The apparatus of claim 17, wherein the suspension component is mounted to a ceiling.

24. The apparatus of claim 17, wherein the suspension component further comprises a constant force balancer, wherein the balancer is a selected one of a group of balancers, the group consisting of:
a) a spring balancer;
b) one or more counterweights;
c) a constant force spring;
d) a pneumatic balancer;
e) an air balancer;
f) a spring motor; and
g) an intelligent assist device.

* * * * *